(12) United States Patent
Chang

(10) Patent No.: US 10,512,683 B2
(45) Date of Patent: Dec. 24, 2019

(54) COMBINATION THERAPIES FOR HUMAN PAPILLOMAVIRUS-ASSOCIATED DISEASES COMPRISING ADMINISTRATION OF THERAPEUTIC VACCINE AND RECOMBINANT VIRUS VECTOR

(71) Applicant: Papivax Biotech Inc., Taipei (TW)

(72) Inventor: Yung-Nien Chang, Taipei (TW)

(73) Assignee: Papivax Biotech Inc., Taipei (TW)

(*) Notice: Subject to any disclaimer, the term of this patent is extended or adjusted under 35 U.S.C. 154(b) by 0 days.

(21) Appl. No.: 15/448,924

(22) Filed: Mar. 3, 2017

(65) Prior Publication Data

US 2018/0250386 A1 Sep. 6, 2018

(51) Int. Cl.
| | |
|---|---|
| *A61K 39/285* | (2006.01) |
| *C07K 14/025* | (2006.01) |
| *C07K 14/47* | (2006.01) |
| *A61K 39/12* | (2006.01) |
| *A61K 39/00* | (2006.01) |

(52) U.S. Cl.
CPC ............ *A61K 39/285* (2013.01); *A61K 39/12* (2013.01); *C07K 14/47* (2013.01); *A61K 2039/5256* (2013.01); *A61K 2039/53* (2013.01); *A61K 2039/54* (2013.01); *C07K 2319/00* (2013.01); *C12N 2710/20034* (2013.01); *C12N 2710/24143* (2013.01)

(58) Field of Classification Search
None
See application file for complete search history.

(56) References Cited

U.S. PATENT DOCUMENTS

| | | | | |
|---|---|---|---|---|
| 5,719,054 A | * | 2/1998 | Boursnell | C07K 14/005 435/320.1 |
| 6,096,869 A | * | 8/2000 | Stanley | A61K 38/208 424/184.1 |

OTHER PUBLICATIONS

Chen et al. Boosting with recombinant vaccinia increases HPV-16 E7-specific T cell precursor frequencies of HPV-16 E7-expressing DNA vaccines, Vaccine 18 (2000) 2015-2022.*
Van der Burg et al. Pre-clinical safety and efficacy of TA-CIN, a recombinant HPV16 L2E6E7 fusion protein vaccine, in homologous and heterologous prime-boost regimens. Vaccine 19 (2001) 3652-3660.*
Peng et al. (Cell Biosci (2016) 6:16; published online: Feb. 25, 2016).*
Borysiewicz et al. A recombinant vaccinia virus encoding human papillomavirus types 16 and 18, E6 and E7 proteins as immunotherapy for cervical cancer. The Lancet 1996, 347: 1523-27.*
Rice et al. Protective Properties of Vaccinia Virus-Based Vaccines: Skin Scarification Promotes a Nonspecific Immune Response That Protects against Orthopoxvirus Disease. Journal of Virology 2014, 88: 7753-7763.*

* cited by examiner

*Primary Examiner* — Nianxiang Zou
(74) *Attorney, Agent, or Firm* — Chieh-Mei Wang

(57) ABSTRACT

The present disclosure relates to a combination therapy comprising a therapeutic vaccine and a recombinant vaccinia virus for treating HPV-associated diseases. The present disclosure further relates to a method of administration of a combination therapy comprising a therapeutic vaccine and a recombinant vaccinia virus for treating HPV associated diseases.

20 Claims, 32 Drawing Sheets

Specification includes a Sequence Listing.

COMBINATION THERAPIES FOR HUMAN PAPILLOMAVIRUS-ASSOCIATED DISEASES COMPRISING ADMINISTRATION OF THERAPEUTIC VACCINE AND RECOMBINANT VIRUS VECTOR

REFERENCE TO AN ELECTRONIC SEQUENCE LISTING

The contents of the electronic sequence listing (US60924_1_ST25.txt; Size: 21 KB; and Date of Creation: Feb. 16, 2017) is herein incorporated by reference in its entirety.

FIELD

The present disclosure relates generally to the treatment of human papillomavirus (HPV) associated diseases. More specifically, the present disclosure relates to a combination therapy comprising a therapeutic vaccine and a recombinant vaccinia virus.

BACKGROUND

HPV is a small, circular, and double-stranded DNA virus belonging to the Papillomaviridae family, having an icosahedral structure and no envelope. There are over 200 different virus types in this group. HPV types appear to be type-specific immunogens in that a neutralizing immunity to infection to one type of papillomavirus does not confer immunity against another type of HPV.

In humans, different HPV types cause distinct diseases. While most HPV infections are benign causing warts on areas of the body including the hands, feet and genitals. HPV has been indicated as the human biologic carcinogen at a higher risk of developing certain types of cancers, comprising penile, vaginal, vulva, anal, and oropharyngeal cancers.

HPV types 1, 2, 3, 4, 7, 10 and 26-29 cause benign warts in both normal and immunocompromised individuals. HPV types 5, 8, 9, 12, 14, 15, 17, 19-25, 36 and 46-50 cause flat lesions in immunocompromised individuals. HPV types 6, 11, 34, 39, 41-44 and 51-55 cause nonmalignant condylomata of the genital or respiratory mucosa. HPV types 6 and 11 are the causative agents for more than 90% of all condyloma (genital warts) and laryngeal papillomas. Other HPV types of particular interest with respect to cancer are types 31, 33, 35, 39, 45, 51, 52, 56, 58, 59, 66 and 68. HPV types 16 and 18 are those which have the highest association with cervical cancer. HPV types 31 and 45 are the types with the next highest association with a cancer risk. HPV types 16 and 18 cause epithelial dysplasia of the genital mucosa and are associated with the majority of in situ and invasive carcinomas of the cervix, vagina, vulva and anal canal.

HPV is perhaps best known for causing nearly 100% of cervical cancer cases, which remains the fourth most-deadly cancer in women worldwide. There are upwards of thirty subtypes of HPV and some of these subtypes have been associated with cervical cancer. Around 80% of cervical cancer cases are associated with HPV types 16 (~60%) and 18 (~20%).

The genome of HPV contains open reading frames (ORFs) called E1-E7 and L1 and L2: "E" means early, and "L" means late. L1 and L2 encode capsid proteins of HPV. The early (E) genes are associated with functions comprising virus replication and cell transformation.

The L1 protein is the major capsid protein having a molecular weight of from 55 to 60 kilo-Dalton (kDa) when measured by polyacrylamide gel electrophoresis. The L2 protein is the minor capsid protein which also has an estimated molecular weight of from 55 to 60 kDa and an apparent molecular weight of from 75 to 100 kDa. Most of the L2 protein is internal to the L1 protein. The L2 proteins are highly conserved among different papillomaviruses, especially the 10 basic amino acids at the C-terminus. The L1 ORF is highly conserved among different papillomaviruses.

HPV prophylactic vaccines have been developed and mainly used as a preventative measure against infectious diseases. Indeed, there have been several successes in the development of the prophylactic vaccines which have effectively prevented healthy, vaccinated patients by or associated with HPV infections, targeting the major capsid protein of the virus-like particles (VLPs). VLPs are morphologically similar to authentic virions and are capable of inducing high titres of neutralizing antibodies upon administration into animals or humans. Because VLPs do not contain the potentially oncogenic viral genome, they present a safe alternative to the use of live virus in HPV vaccine development. For this reason, the L1 and L2 genes have been identified as immunological targets for the development of prophylactic and therapeutic vaccines for HPV infections and associated diseases.

After HPV viral DNA is integrated in to the host's genome, the early genes (E1, E2, E4 and, E5) and the late genes (L1 and L2) can be deleted. The E2 gene is a negative regulator for HPV oncogenes E6 and E7; therefore, these oncogenes serve as a hallmark of HPV-associated diseases because they are often expressed at elevated levels in infected cells. The oncoproteins E6 and E7 are functionally required for the initiation and maintenance of the diseases and serve as non-self, foreign proteins. For these reasons, the oncoproteins E6 and E7 have received significant attention as ideal targets for HPV therapeutic vaccines.

VLP-based vaccines have proven to be effective at inducing immune responses in human patients vaccinated with bivalent HPV types 16 and 18 prophylactic vaccines, quadrivalent HPV types 6, 11, 16, and 18 VLP-based vaccines, and nine-valent HPV types 6, 11, 16, 18, 31, 33, 45, 52, and 58 prophylactic vaccines. For example, CERVARIX, GARDASIL® and GARDASLL® 9 are available polyvalent vaccines marketed for prevention of HPV.

CERVARIX is a bivalent prophylactic vaccine indicated for the prevention of HPV (types 16 and 18). CERVARIX is approved for use in females 9 through 25 years of age for the prevention of cervical cancer, cervical intraepithelial neoplasia or worse and adenocarcinoma in situ caused by HPV types 16 and 18. However, CERVARIX has not been demonstrated to provide protection against disease from vaccine and non-vaccine HPV types to which a woman has previously been exposed through sexual activity.

GARDASIL® is a commercially available quadrivalent prophylactic vaccine having activity against HPV (types 6, 11, 16, and 18). GARDASIL® is indicated in girls and women 9 through 26 years of age for the prevention of cervical, vulvar, vaginal, and anal cancer caused by HPV types 16 and 18, genital warts caused by HPV types 6 and 11, and cervical intraepithelial neoplasia, cervical adenocarcinoma in situ, cervical intraepithelial neoplasia, vulvar intraepithelial neoplasia, vaginal intraepithelial neoplasia, anal intraepithelial neoplasia caused by HPV types 6, 11, 16, and 18. GARDASIL® is also indicated in boys and men 9 through 26 years of age for the prevention of anal cancer caused by HPV types 16 and 18, genital warts caused by HPV types 6 and 11, and anal intraepithelial neoplasia caused by HPV types 6, 11, 16, and 18.

GARDASIL® 9 is another commercially available nine-valent vaccine marketed for prevention of HPV (types 6, 11, 16, 18, 31, 33, 45, 52, and 58). GARDASIL® 9 is indicated in girls and women 9 through 26 years of age for the prevention of cervical, vulvar, vaginal, and anal cancer caused by HPV types 16, 18, 31, 33, 45, 52, and 58, genital warts caused by HPV types 6 and 11, and cervical intraepithelial neoplasia, cervical adenocarcinoma in situ, cervical intraepithelial neoplasia, vulvar intraepithelial neoplasia, vaginal intraepithelial neoplasia, anal intraepithelial neoplasia caused by HPV types 6, 11, 16, 18, 31, 33, 45, 52, and 58. GARDASIL® 9 is also indicated in boys and men 9 through 26 years of age for the prevention of anal cancer caused by HPV types 16, 18, 31, 33, 45, 52, and 58, genital warts caused by HPV types 6 and 11, and anal intraepithelial neoplasia caused by HPV types 6, 11, 16, 18, 31, 33, 45, 52, and 58.

These preventive vaccines are typically administered for systemic action, being injected into a patient subcutaneously or intramuscularly (e.g., deltoid), remote from any particular target, such as the cervix. Moreover, they are generally accepted to be effective prior to exposure to HPV and are not commonly known to be effective for treatment after exposure to, or infection with, HPV.

There are limited treatment options for patients with established HPV infections and associated diseases. In addition, the HPV infections remain extremely common globally, representing a significant health burden. Therefore, there is an urgent need to develop effective and innovative treatments to clear HPV infections and HPV-associated diseases.

HPV antigen-derived proteins are processed by dendritic cells (DCs) and presented by major histocompatibility complex (MHC) class I or class II molecules to initiate CD8+ or CD4+ T cell immune responses, respectively. Protein-based vaccines have been shown to be safe and easy to produce.

The present disclosure relates to a combination therapy comprising a therapeutic vaccine and a recombinant vaccinia virus for treating HPV-associated diseases. The present disclosure further relates to a method of administration of a combination therapy comprising a therapeutic vaccine and a recombinant vaccinia virus for treating HPV associated diseases.

BRIEF DESCRIPTION OF THE DRAWINGS

Implementations of the present technology will now be described, by way of example only, with reference to the attached figures. Many aspects of the present disclosure can be better understood with reference to the following figures. The components in the figures are not necessarily drawn to scale with the emphasis instead being placed upon clearly illustrating the principles of the present disclosure.

DETAILED DESCRIPTION

Figure 1A:
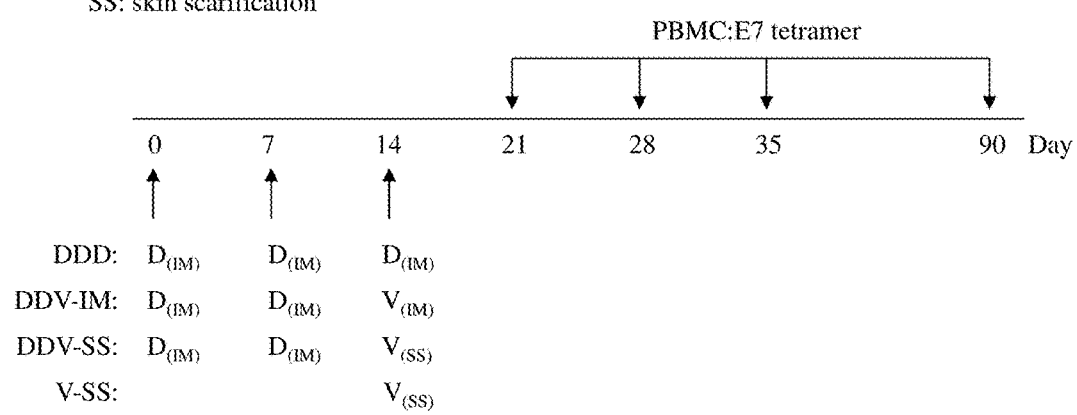
FIG. 1A shows boosting of pNGVL4a-sig/E7(detox)/HSP70 DNA vaccine vaccination by TA-HPV administration in naïve C57BL/6 mice, as described in EXAMPLE 1.

It will be appreciated that for simplicity and clarity of illustration, where appropriate, reference numerals have been repeated among the different figures to indicate corresponding or analogous elements. In addition, numerous specific details are set forth in order to provide a thorough understanding of the examples described herein. However, it will be understood by those of ordinary skill in the art that the examples described herein can be practiced without these specific details. In other instances, methods, procedures and components have not been described in detail so as not to obscure the related relevant feature being described. The drawings are not necessarily to scale and the proportions of certain parts may be exaggerated to better illustrate details and features. The description is not to be considered as limiting the scope of the examples described herein.

Several definitions that apply throughout this disclosure will now be presented.

The term "comprising" or "containing" when utilized, means "including, but not necessarily limited to"; it specifically indicates open-ended inclusion or membership in the so-described combination, group, series and the like. The term "administering", "administration" and "administered" are the dispensing of a therapeutic agent to treat a condition, which is usually given orally, intravenously, parenterally, subcutaneously, intraperitoneally, intramuscularly, anally, mucosally, intravaginally, intranasally, intralesional, via inhalation or skin scarification, added to an intravenous line ("drip"), or painted on the skin or mucosa. The term "applying" is the act of bringing something into contact or of starting an action. The term "dosage form" is pharmaceutical drug products in the form in which they are marketed for use in a particular configuration with a specific mixture of active ingredients and excipients, and apportioned into a particular dose. The term "infect" or "infection" are the invasion of bodily tissue by pathogenic microorganisms that proliferate, resulting in tissue injury that can progress to disease. The term "immunity" is the ability of an organism to resist a particular infection or toxin by the action of specific antibodies or sensitized white blood cells. The term "against" means a defense or a safeguard from pathogens infections or diseases. The term "immunocompromised" means an impaired immune system and therefore incapable of an effective immune response. The term "in situ" is means something that is in its original place. The term "in vitro" is tests or experiments are made to occur in a laboratory vessel or other controlled experimental environment rather than within a living organism or natural setting. The term "in vivo" is tests or experiments are occurring or made to occur within a living organism or natural setting. The term "open reading frame" is the part of a reading frame that has the potential to be translated in molecular genetics. An open reading frame is a continuous stretch of codons that do not contain a stop codon. The "prophylactic" is intended to prevent disease, relating to prophylaxis or prevention.

The term "carcinogen" means a substance capable of causing cancer in living tissue. The term "oncogene" means a gene that in certain circumstances can transform a cell into a tumor cell. The term "oncoprotein" means a protein encoded by an oncogene which can cause the transformation of a cell into a tumor cell if introduced into it. The term "wart" is a small, hard, growth on the skin, caused by a virus infection. The term "condyloma" is a raised growth on the skin resembling a wart, typically in the genital region, and transmissible by contact. The term "papilloma" is a small wart-like growth on the skin or on a mucous membrane, derived from the epidermis. The term "dendritic cell" is an antigen-presenting leukocyte found in the skin, mucosa, and lymphoid tissue that initiates a primary immune-response by activating lymphocytes and secreting cytokines. The term "major histocompatibility complex" is a set of cell surface proteins essential for the acquired immune system to recognize foreign molecules in vertebrates, which in turn determines histocompatibility. The main function of major histocompatibility complex molecules is to bind to peptide fragments derived from pathogens and display them on the cell surface for recognition by the appropriate T-cells. The term "T cell" is a lymphocyte of a type produced or processed by the thymus gland and actively participating in the immune response. The term "apoptosis" is a process of programmed cell death that occurs in multicellular organisms. The term "antibody" as used herein includes both polyclonal and monoclonal antibodies, as well as fragments thereof, such as, Fv, Fab and F(ab)2 fragments that are capable of binding antigen or hapten. The term "pfu", plaque-forming unit, is a measure of the number of particles capable of forming plaques per unit volume, such as virus particles. It is a functional measurement rather than a measurement of the absolute quantity of particles: viral particles that are defective or which fail to infect their target cell will not produce a plaque and thus will not be counted. The term "combination" in the present disclosure is the act of combining separate entities by joining, uniting, or otherwise bringing into close association. The term "combination therapy" in the present disclosure means the use of multiple drugs or other agents as part of a treatment regimen against a specific disease to improve effectiveness, prevent the development of drug resistance, and minimize side effects. The term "therapeutic response" is a consequence of a medical treatment, the results of which are judged to be desirable and beneficial. The term "prime-boost regimen" in the present disclosure refers to a vaccination strategy adopting multiple immunizations that comprise at least one early immunization as a prime and at least one late immunization as a boost. The term "heterologous prime-boost regimen" in the present disclosure refers to a prime-boost regimen that comprises different vaccines used separately as the prime and the boost.

INTRODUCTION

Papillomavirus infections occur in a variety of animals, including humans, sheep, dogs, cats, rabbits, monkeys, snakes, mice, cows and other mammals. Papillomaviruses infect epithelial cells, generally inducing benign epithelial or fibroepithelial tumors at the site of infection. Papillomaviruses may be classified into distinct groups based on the host that they infect.

Human papillomavirus (HPV) is a small, circular, and double-stranded DNA virus belonging to the Papillomaviridae family, having an icosahedral structure and no envelope. There are over 200 different virus types in this group. HPV types appear to be type-specific immunogens in that a neutralizing immunity to infection to one type of papillomavirus does not confer immunity against another type of HPV.

In humans, different HPV types cause distinct diseases. Such diseases are called HPV-associated diseases. While most HPV infections are benign causing warts on areas of the body including the hands, feet and genitals. HPV has been indicated as the human biologic carcinogen at a higher risk of developing certain types of cancers, comprising penile cancer, vaginal cancer, vulva cancer, anal cancer, oropharyngeal cancer, non-melanoma skin cancer, conjunctival cancer or cervical cancer.

HPV types 1, 2, 3, 4, 7, 10 and 26-29 cause benign warts in both normal and immunocompromised individuals. HPV types 5, 8, 9, 12, 14, 15, 17, 19-25, 36 and 46-50 cause flat lesions in immunocompromised individuals. HPV types 6, 11, 34, 39, 41-44 and 51-55 cause nonmalignant condylomata or intraepithelial neoplasia of the genital or respiratory mucosa. HPV types 6 and 11 are the causative agents for more than 90% of all condyloma (genital warts) and laryngeal papillomas. Other HPV types of particular interest with respect to cancer are types 31, 33, 35, 39, 45, 51, 52, 56, 58, 59, 66 and 68. HPV types 16 and 18 are those which have the highest association with cervical cancer. HPV types 31 and 45 are the types with the next highest association with a cancer risk. HPV types 16 and 18 cause epithelial dysplasia of the genital mucosa and are associated with the majority of in situ and invasive carcinomas of the cervix, vagina, vulva and anal canal.

HPV is perhaps best known for causing nearly 100% of cervical cancer cases, which remains the fourth most-deadly cancer in women worldwide. There are upwards of thirty subtypes of HPV and some of these subtypes have been associated with cervical cancer. Around 80% of cervical cancer cases are associated with HPV types 16 (~60%) and 18 (~20%).

The genome of HPV contains open reading frames (ORFs) called E1-E7 and L1 and L2: "E" means early, and "L" means late. L1 and L2 encode capsid proteins of HPV. The early (E) genes are associated with functions such as virus replication and cell transformation.

The L1 protein is the major capsid protein having a molecular weight of from 55 to 60 kilo Dalton (kDa) when measured by polyacrylamide gel electrophoresis. The L2 protein is the minor capsid protein which also has an estimated molecular weight of from 55 to 60 kDa and an apparent molecular weight of from 75 to 100 kDa. Most of the L2 protein is internal to the L1 protein. The L2 proteins are highly conserved among different papillomaviruses, especially the 10 basic amino acids at the C-terminus. The L1 ORF is highly conserved among different papillomaviruses.

HPV prophylactic vaccines have been developed and mainly used as a preventative measure against infectious diseases. Indeed, there have been several successes in the development of the prophylactic vaccines which have effectively prevented healthy, vaccinated patients by or associated with HPV infections, targeting the major capsid protein of the virus-like particles (VLPs). VLPs are morphologically similar to authentic virions and are capable of inducing high titres of neutralizing antibodies upon administration into animals or humans. Because VLPs do not contain the potentially oncogenic viral genome, they present a safe alternative to the use of live virus in HPV vaccine development. For this reason, the L1 and L2 genes have been identified as immunological targets for the development of prophylactic vaccines for HPV infection.

After HPV viral DNA is integrated in to the host's genome, the early genes (E1, E2, E4 and, E5) and the late genes (L1 and L2) can be deleted. The E2 gene is a negative regulator for HPV oncogenes E6 and E7. If E2 is typically destroyed when the viral genome integrates it results in expression of the viral oncogenes E6 and E7 in the host cells and cell transformation. The oncoproteins E6 and E7 are functionally required for the initiation and maintenance of the diseases. Therefore, these viral oncogenes serve as a hallmark of HPV-associated diseases because they are often expressed at elevated levels in infected cells. For these reasons, the HPV oncoproteins E6 and E7 have received significant attention as ideal targets for HPV therapeutic vaccines.

The preventive vaccines are typically administered for systemic action, being injected into a patient subcutaneously or intramuscularly (e.g., deltoid), remote from any particular target, such as the cervix. Moreover, they are generally accepted to be effective prior to exposure to HPV and are not commonly known to be effective for treatment after exposure to, or infection with, HPV.

There are limited treatment options for patients with established HPV infections and associated diseases. In addition, the HPV infections remain extremely common globally, representing a significant health burden. Therefore, there is an urgent need to develop effective and innovative treatments to clear HPV infections and HPV-associated diseases.

Strategies to treat existing HPV infections and HPV-associated diseases have experienced a great encouragement with the developments of therapeutic HPV vaccines candidates. One emergent therapeutic HPV vaccine type is a DNA vaccine. Therapeutic HPV DNA vaccines encode E6 and/or E7 antigens into a plasmid DNA, which is then injected into the host cells upon vaccination. One benefit to using DNA vaccines is that they do not lead to antibodies that prevent effective repeat administration. One concern for therapeutic HPV DNA vaccine is that administering DNA encoding HPV oncogenes E6 and E7 runs the risk of initiating cellular transformation. To address this risk, the HPV oncogenes E6 and E7 DNA are modified by mutation to express proteins that are incapable of oncogenic transformation, here termed a "detox" form. Alternatively, dendritic cells (DCs) play an important role in antigen presentation to CD8+ cytotoxic T cells, and can present the antigens encoded in the DNA vaccine either through direct transfection of the plasmid DNA and subsequently expressing the encoded antigen, or by taking up the antigens expressed and released by the myocytes and present the antigens through cross presentation pathway. Another potential limitation associated with DNA vaccines is their low immunogenicity. Naked DNA is unable to amplify and spread from transfected cells to surrounding cells and amplify the antigen expression.

To enhance the therapeutic efficacy of the therapeutic DNA vaccine, vaccinia virus is developed to enhance the immune responses generated by DNA vaccination. Vaccinia virus is a double-stranded DNA virus belonging to the Poxvirus family. It is often used as a viral vector because it is extremely infectious and has a low likelihood of irregular DNA integration into the host's genome.

A live recombinant vaccinia virus, TA-HPV, is expressing HPV types 16 and 18 oncoproteins E6 and E7. The TA-HPV is used alone or in a prime-boost regimen to enhance the immune response of several heterologous vaccines, including the TA-HPV and the DNA vaccines in the present disclosure.

Both the TA-HPV and the DNA vaccines are often administered via intramuscular (IM) injection. Although this is a traditional administration route, it is still unclear what the best route of administration for either of these vaccines might be.

The TA-HPV and the DNA vaccines or a combination thereof may be administered by a variety of routes comprising orally, intranasally, intravenously, parenterally, subcutaneously, intraperitoneally, anally, intravaginally, intramuscularly, intralesional, via skin scarification, painted on the skin, intradermally, mucosally, or added to a "drip".

The dosage administered may vary with the condition, sex, weight, age of the individual, the route of administration, and the HPV type vaccine. The vaccine may be used in dosage form comprising capsule, suspension, elixir, freeze dried and liquid solution. The capsule is an enclosing structure, usually as a solid dosage form in which a drug is enclosed in a hard or soft soluble container or "shell" of a suitable form of gelatin. The suspension is a heterogeneous mixture containing solid particles that are sufficiently large for sedimentation. The elixir is a clear, sweetened, hydroalcoholic liquid intended for oral use, usually contains flavoring substances and is used either as vehicles or for the therapeutic effect of the active medicinal agents. Freeze dried product is in a desiccated powder format such that the vaccine can be viably or functionally recovered upon addition of dissolving aqueous medium. The liquid solution is a homogeneous mixture composed of two or more substances (solutes) dispersed molecularly in a sufficient quantity of dissolving liquid medium (solvent).

The vaccine may be formulated with an immunologically acceptable carrier. The vaccines are administered in therapeutically preferable amounts, that is, in amounts sufficient to generate an immunologically protective response. The therapeutically preferable amount may vary according to the type of HPV. The vaccine may be administered in single or multiple doses. The vaccine may be administered by a needle (single or multiple) alone and in the case of a case DNA vaccine in combination with electroporation, or excipients that promote in vivo transduction.

In the present disclosure, the therapeutic efficacy of heterologous DNA vaccines prime, recombinant vaccinia virus boosted vaccination regimen in a TC-1 tumor model is examined. In addition, the optimal route of the vaccinia virus vaccination to elicit the most potent antitumor immune response is disclosed.

The DNA vaccine may be selected from a pcDNA3-CRT DNA vaccine, a pcDNA3-CRT/HPV16E7 DNA vaccine, a pcDNA3-CRT/HPV18E6 DNA vaccine, a pNGVL4a-CRT/HPV16E7(detox) DNA vaccine, a pNGVL4a-CRT/HPV18E6 DNA vaccine, a pNGVL4a-CRT/E6E7L2 DNA vaccine or a pNGVL4a-sig/E7(detox)/HSP70 DNA vaccine. The pcDNA3-CRT DNA vaccine is consisting of the coding sequences of a pcDNA3 vector and a calreticulin (CRT). The pcDNA3-CRT/HPV16E7 DNA vaccine is consisting of the coding sequences of a pcDNA3 vector and a CRT fused to a HPV16 E7 protein. The pcDNA3-CRT/HPV18E6 DNA vaccine is consisting of the coding sequences of a pcDNA3 vector and a CRT fused to a HPV18 E6 protein. The pNGVL4a-CRT/HPV16E7(detox) DNA vaccine is consisting of the coding sequences of a CRT fused to a detox form of a HPV16 antigen E7. The pNGVL4a-CRT/HPV18E6 DNA vaccine is consisting of the coding sequences of a CRT fused to the HPV18 E6 protein. The pNGVL4a-CRT/E6E7L2 DNA vaccine is consisting of the coding sequences of a CRT fused to the HPV16 E6, E7 and L2 proteins. The pNGVL4a-sig/E7(detox)/HSP70 DNA vaccine is consisting of the coding sequences of a signal peptide (sig), a detox form of a HPV antigen E7, and a heat shock protein 70 (HSP70). The DNA vaccine may be administered in dosages ranging from 1 microgram per subject (µg/subject) to 50 milligram per subject (mg/subject); the DNA vaccine may be administered preferably in dosages ranging from 500 µg/subject to 20 mg/subject; the DNA vaccine may be administered further preferably in dosage 1 mg/subject to 10 mg/subject. The subject may comprise human, mouse, sheep, dog, cat, rabbit, monkey, snake, cow or other mammals.

The TA-HPV is a recombinant vaccinia viral vaccine, expressing HPV types 16 and 18 oncogenes E6 and E7. The HPV types 16 and 18 oncogenes E6 and E7 are inserted in a head-to-head orientation under the control of the p7.5 and H6 promoters at a neutral site in the vaccinia virus Wyeth strain genome. For both the HPV types 16 and 18 genes, the E6 termination codon is altered to create an E6/E7 fused open reading frame and defined mutation introduced to inactivate the Rb-binding site in E7. The recombinant viral vaccine may be administered in dosages ranging from $1 \times 10^4$ pfu to $5 \times 10$ pfu; the vaccinia recombinant viral vaccine may be administered preferably in dosages ranging from $2 \times 10^4$ pfu to $5 \times 10^7$ pfu.

The present disclosure relates to enhance the immune responses generated by a combination therapy comprising a therapeutic vaccine and a recombinant vaccinia virus. In addition, the present disclosure relates to the optimal route of the recombinant vaccinia virus vaccination to elicit the most potent antitumor immune response. Furthermore, the present disclosure is the first to treat HPV E6/E7-expressing tumor using a combination therapy comprising a therapeutic vaccine and a recombinant vaccinia virus.

Material and Methods 5-8 weeks old female naïve C57BL/6 mice are purchased from Charles River Laboratories (Frederick, Md.). All mice are maintained at Johns Hopkins University School of Medicine Oncology Animal Facility (Baltimore, Md.) under specific-pathogen-free conditions. All procedures are performed according to protocols approved by the Johns Hopkins Institutional Animal Care and Use Committee and in accordance with recommendations for the proper use and care of laboratory animals.

HPV16 E7aa49-57 peptide and HPV18 E6aa67-75 peptide are synthesized by GenScript (Piscataway, N.J.) at a purity of ≥80%. PE-conjugated anti-mouse CD8a antibody (clone: 53.6.7), FITC-conjugated anti-mouse IFN-γ antibody (clone: XMG1.2), purified anti-mouse CD16/32 antibody (Fc Block™), and 7-Amino-Actinomycin D (7-AAD) are purchased from BD Pharmingen (BD Pharmingen, San Diego, Calif.). Purified anti-HPV16 E7 monoclonal antibody (clone 8C9) is purchased from Thermo Scientific (Rockford, Ill.). PE-conjugated, HPV16 E7aa49-57 peptide loaded H2-D$^b$ tetramers are obtained from the National Institute of Allergy and Infectious Diseases Tetramer Facility (Atlanta, Ga.). G-418 disulfate salt is purchased from Sigma-Aldrich (St. Louis, Mo.). Purified HPV16 E7 protein is purchased from Protein X Lab (San Diego, Calif.). Bifurcated needles are purchased from Precision Medical Products, INC (Denver, Pa.).

The TC-1 cell is an HPV type 16 E6/E7-expressing murine tumor cell line. The TC-1 cell expressing the firefly luciferase gene (TC-1/luc) is developed. The TC-1 cell is tumorigenic in syngeneic and immunocompetent mice, the mice has been characterized as a model for human cervical carcinoma. The TC-1 cells are maintained in RPMI medium supplemented with 2 mM glutamine, 1 mM sodium pyruvate, 100 IU/mL penicillin, 100 µg/mL streptomycin, 400 µg/mL of G-418 and 10% fetal bovine serum (FBS).

The DNA vaccines comprise a pcDNA3-CRT DNA vaccine, a pcDNA3-CRT/HPV16E7 DNA vaccine, a pcDNA3-CRT/HPV18E6 DNA vaccine, a pNGVL4a-CRT/HPV16E7 (detox) DNA vaccine, a pNGVL4a-CRT/HPV8E6 DNA vaccine, a pNGVL4a-CRT/E6E7L2 DNA vaccine or a pNGVL4a-sig/E7(detox)/HSP70 DNA vaccine. The TA-HPV expresses HPV types 16 and 18 oncogenes E6 and E7. The recombinant vaccinia expressing luciferase (Lister strain, rVV4) and wild-type vaccinia virus (WR strain) are used.

For the DNA vaccines vaccination, the DNA vaccines are prepared in 50 microliter (µL) and injected intramuscularly (biceps femoris muscle). The DNA vaccines are prepared using endotoxin-free kit (Qiagen) and injected into biceps femoris muscle in 50 µL. For the TA-HPV intramuscular vaccination, the mice are injected with the TA-HPV (50 µL) intramuscularly (biceps femoris muscle). For the TA-HPV skin scarification, 5 µL of the TA-HPV is applied to the mice tail skin at 1 cm from the base of tail, on buttock, on hind leg (thigh), on ear, or on arm. The skin area is then gently scratched 15 times with a bifurcated needle. The administration of the TA-HPV at the tail, on the buttock or on the thigh may treat anogenital HPV diseases. The administration of the TA-HPV on the arm or on the ear may treat head and neck-related HPV diseases.

The CRT inserted sequence of pcDNA3-CRT DNA vaccine, the CRT/HPV16E7 inserted sequence of pcDNA3-CRT/HPV16E7 DNA vaccine, the CRT/HPV18E6 inserted sequence of pcDNA3-CRT/HPV18E6 DNA vaccine, the pNGVL4a-CRT/HPV16E7(detox) DNA vaccine sequence, the pNGVL4a-CRT/HPV8E6 DNA vaccine sequence, the pNGVL4a-CRT/E6E7L2 DNA vaccine sequence, the pNGVL4a-sig/E7(detox)/HSP70 DNA vaccine sequence, the inserted sequence in TA-HPV, the HPV16 E7aa49-57 peptide sequence and the HPV18 E6aa67-75 peptide sequence are shown in sequence listing.

The table 1 shows SEQ ID NOs and the corresponding DNA vaccines and peptides.

TABLE 1

| SEQ ID NO: | Corresponding DNA vaccines and peptides |
|---|---|
| 1 | CRT inserted sequence of pcDNA3-CRT DNA vaccine |
| 2 | CRT/HPV16E7 inserted sequence of pcDNA3-CRT/HPV16E7 DNA vaccine |
| 3 | CRT/HPV18E6 inserted sequence of pcDNA3-CRT/HPV18E6 DNA vaccine |
| 4 | pNGVL4a-CRT/HPV16E7(detox) DNA vaccine |
| 5 | pNGVL4a-CRT/HPV18E6 DNA vaccine |
| 6 | pNGVL4a-CRT/E6E7L2 DNA vaccine |
| 7 | pNGVL4a-sig/E7(detox)/HSP70 DNA vaccine |
| 8 | Inserted sequence in TA-HPV |
| 9 | HPV16 E7aa49-57 peptide |
| 10 | HPV18 E6aa67-75 peptide |

For tetramer staining, peripheral blood mononucleocytes (PBMCs) from the mice were stained with purified anti-mouse CD16/32 firstly, and then stained with anti-mouse CD8-FITC, and PE-conjugated H-2D$^b$ tetramer loaded with HPV16 E7aa49-57 peptide at 4° C. After washing, the cells are stained with 7-AAD before flow cytometry analysis to exclude dead cells. The cells are acquired with FACSCalibur flow cytometer and analyzed with CellQuest Pro software.

To detect HPV16 E7 and HPV18 E6-specific CD8+ T cell responses by IFN-γ intracellular staining, splenocytes of the mice are stimulated with either HPV16 E7aa49-57 or HPV18 E6aa67-75 peptide (1 μg/mL) at the presence of GolgiPlug (BD Pharmingen, San Diego, Calif.) at 37° C. overnight. The stimulated splenocytes are then washed once with phosphate buffered saline (PBS) containing 0.5% bovine serum albumin (BSA) and stained with PE-conjugated anti-mouse CD8 antibody. The splenocytes are permeabilized and fixed with Cytofix/Cytoperm kit according to the manufacturer's instruction (BD Pharmingen, San Diego, Calif.). Intracellular IFN-γ is stained with FITC-conjugated rat antimouse IFN-γ. Flow cytometry analysis is performed using FACSCalibur flow cytometer with CellQuest Pro software (BD biosciences, Mountain View, Calif.).

HPV16 E7-specific antibody response is detected by an enzyme-linked immunoabsorbent assay (ELISA). Optical density (OD) value is read with xMark Microplate Spectrophotometer (BioRad, Hercules, Calif.) ELISA reader at 405 nm.

The expression of luciferase by inoculated vaccinia virus or the TC-1/luciferase tumor cells is monitored by bioluminescence using a Xenogen imaging system. Mice are given D-Luciferin by intraperitoneally (i.p.) injection (200 microliter per mouse (μL/mouse), 75 milligram per kilogram (mg/kg)) and anesthetized with isoflurane. In vivo bioluminescence imaging for luciferase expression is conducted on a cryogenically cooled IVIS system using Living Image acquisition and analysis software (Xenogen). The mice are placed onto the warmed stage inside the light-tight camera box with continuous exposure to 1%-2% isoflurane. Images are acquired 10 minutes after D-luciferin administration and imaged for appropriate time. The levels of light from the bioluminescent cells are detected by the IVIS imager, integrated, and digitized. The region of interest from displayed images is designated and quantified as total photon counts using Living Image 2.50 software (Xenogen).

For the in vivo tumor protection experiment, the female naïve C57BL/6 mice are separated into four groups (five mice per group). One group of the naïve C57BL/6 mice is vaccinated with PBS as a blank control. Another group of the naïve C57BL/6 mice is vaccinated with 25 microgram per mouse (μg/mouse) of pNGVL4a-sig/E7(detox)/HSP70 DNA (50 μL) through intramuscular injection of the thigh muscle and boosted with the same regimen once with two weeks interval. Another group of the naïve C57BL/6 mice is vaccinated with 25 μg/mouse of pNGVL4a-sig/E7(detox)/HSP70 DNA (50 μL) through intramuscular injection of the thigh muscle and boosted once with the same regimen with two weeks interval, and at two weeks later further boosted with 5×10$^5$ pfu of the TA-HPV through skin scarification on the tail. Two weeks before the TC-1/luciferase tumor cells injected, the last group of the naïve C57BL/6 mice is vaccinated with 5×10$^5$ pfu of the TA-HPV through skin scarification on the tail. Two weeks after the treatment administration, all groups of the naïve C57BL/6 mice are injected with 1×10$^5$ of TC-1/luciferase tumor cells intravaginally. The growth of the tumor is monitored by the expression of luciferase with bioluminescence using a Xenogen imaging system.

For the in vivo tumor treatment experiment, the female naïve C57BL/6 mice (five per group) are injected with 2×10$^4$ of TC-1/luciferase tumor cells intravaginally. The first day after tumor cells injection, one group of TC-1/luciferase tumor cell challenged mice is vaccinated with PBS as a blank control. Another group of TC-1/luciferase tumor cell challenged mice is vaccinated with 25 μg/mouse of pNGVL4a-sig/E7(detox)/HSP70 DNA (50 μL) through intramuscular injection at the thigh muscle and boosted twice with the same regimen with 4-day interval. Another group of the TC-1/luciferase tumor cell challenged is vaccinated with 25 μg/mouse of pNGVL4a-sig/E7(detox)/HSP70 DNA (50 ILL) through intramuscular injection at the thigh muscle and boosted once with the same regimen with 4-day interval, and further boosted with 5×10$^5$ pfu of TA-HPV vaccinia virus through skin scarification on the tail at the ninth day after the TC-1/luciferase tumor cell injection. Another group of the TC-1/luciferase tumor cell challenged mice is vaccinated with 25 g/mouse of pNGVL4a-sig/E7(detox)/HSP70 DNA (50 μL) through intramuscular injection at front leg muscle and boosted once with the same regimen with 4-day interval, and further boosted with 5×10$^5$ pfu of TA-HPV vaccinia virus through skin scarification on the ear at the ninth day after the TC-1/luciferase tumor cell injection. The last group of the TC-1/luciferase tumor cell challenged mice is vaccinated with 5×10$^5$ pfu of TA-HPV vaccinia virus through skin scarification on the tail at the ninth day after the TC-1/luciferase tumor cell injection. The growth of the tumor was monitored by the expression of luciferase with bioluminescence using a Xenogen imaging system.

All data are expressed as means±standard deviations (SD). Comparisons between individual data point is analyzed by 2-tailed Student's t test. The non-parametric Mann-Whitney test was used for comparing two different groups. Survival distributions for mice in different groups are compared by the Kaplan-Meier curves and by use of the long-rank tests. A p value of less than 0.05 is considered significant.

Example 1

Figure 1B:
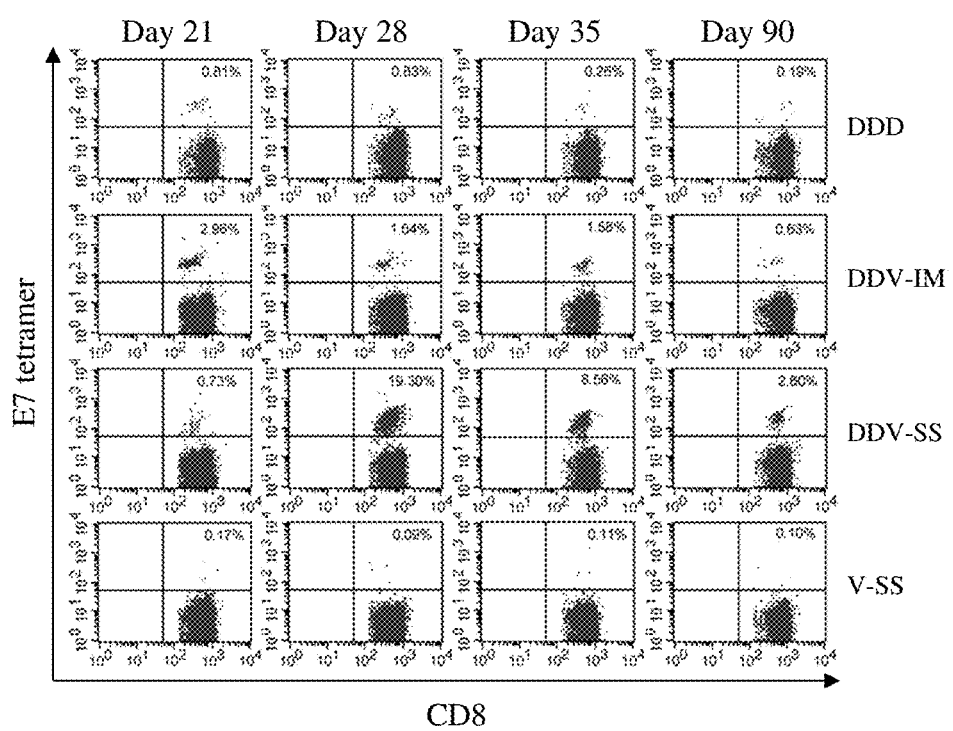
FIG. 1B shows representative flow cytometry analysis of E7 tetramer-stained PBMC taken from groups of naïve C57BL/6 mice that had been immunized as described in FIG. 1A and illustrates that TA-HPV administration boosted pNGVL4a-sig/E7(detox)/HSP70 DNA vaccine vaccination, as described in EXAMPLE 1.
Figure 1C:
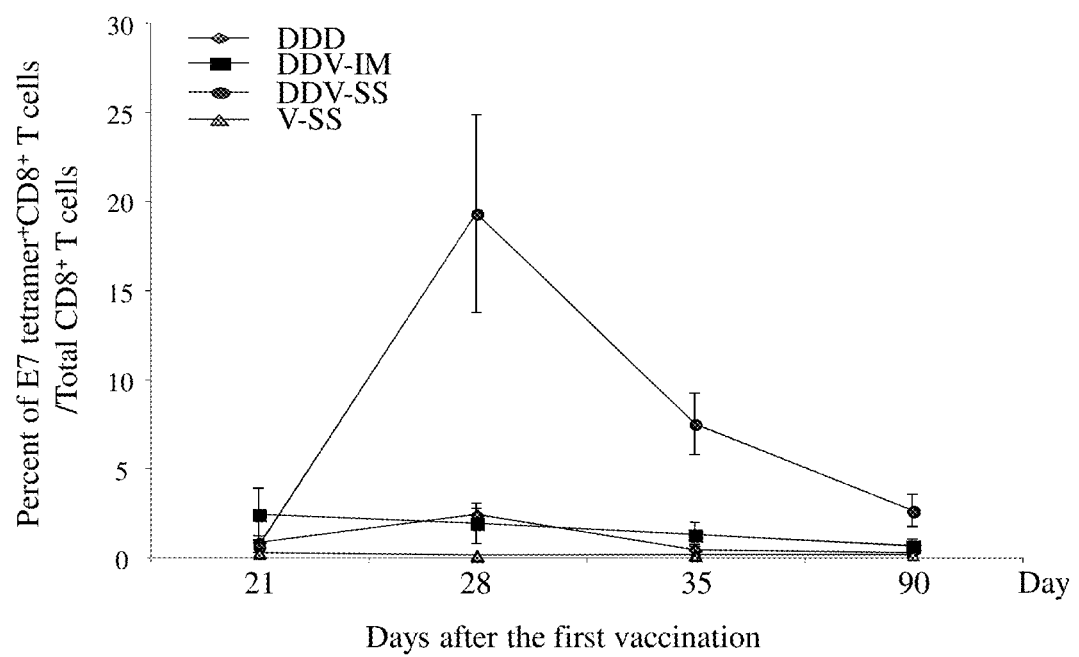
FIG. 1C is a summary of flow cytometry analysis of E7 tetramer-stained PBMC taken from groups of naïve C57BL/6 mice that had been immunized as described in FIG. 1A and illustrates that TA-HPV administration boosted pNGVL4a-sig/E7(detox)/HSP70 DNA vaccine vaccination, as described in EXAMPLE 1.

To evaluate the immune response of the 5-8 week old female naïve C57BL/6 mice elicited by different vaccination regimen and route of vaccination, there are four vaccination regimens comprising 1) intramuscular (IM) pNGVL4a-sig/E7(detox)/HSP70 DNA vaccine injection in the thigh on day 0, boosted with the same vaccination on day 7 and day 14 (DDD); 2) IM pNGVL4a-sig/E7(detox)/HSP70 DNA vaccine injection in the thigh on day 0, boosted with the same vaccination on day 7, and vaccinated with TA-HPV via IM injection on day 14 (DDV-IM); 3) IM pNGVL4a-sig/E7(detox)/HSP70 DNA vaccine injection in the thigh on day 0, boosted with the same vaccination on day 7, and vaccinated with TA-HPV on the tail via skin scarification on day 14 (DDV-SS); or 4) IM PBS treatment in the thigh on day 0 and day 7, and vaccinated with TA-HPV on the tail via skin scarification on day 14 (V-SS). PBMCs are then prepared on day 21, 28, 35 and 90 (FIG. 1A), and stained with anti-mouse CD8 and HPV16 E7 tetramer, and analyzed using flow cytometry. As shown in FIGS. 1B and 1C, the mice administered with DDV-SS vaccination regimen show the most robust HPV16 E7-specific CD8+ T cell response, while the mice vaccinated with all other regimens show similar and weak HPV16 E7-specific CD8+ T cell responses. Furthermore, the mice administered with DDV-SS vaccination regimen show a long-lasting HPV16 E7-specific CD8+ T cell response and reaching the highest level on day 28 before the response starts to decrease, but the response continues to remain higher than the background even at 90 days after the first vaccination (FIG. 1C).

Figure 1D:
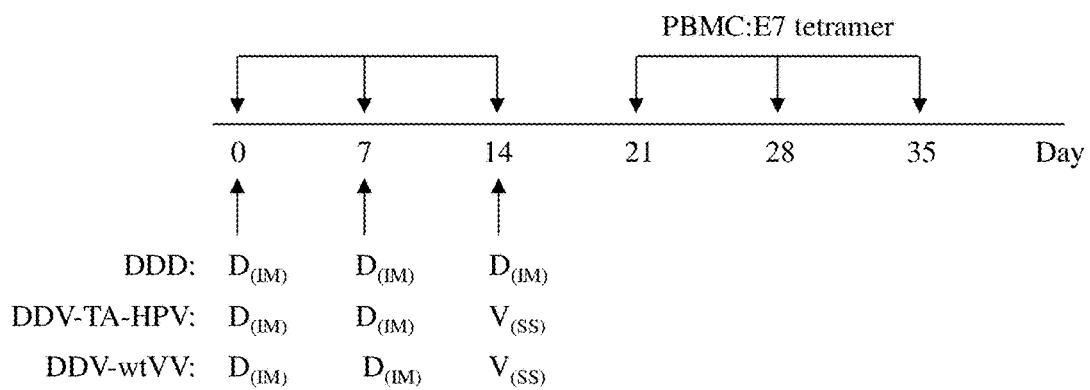
FIG. 1D shows TA-HPV or wild-type vaccinia virus (wtVV) administration boosted pNGVL4a-sig/E7(detox)/HSP70 DNA vaccine vaccination in naïve C57BL/6 mice, as described in EXAMPLE 1.
Figure 1E:
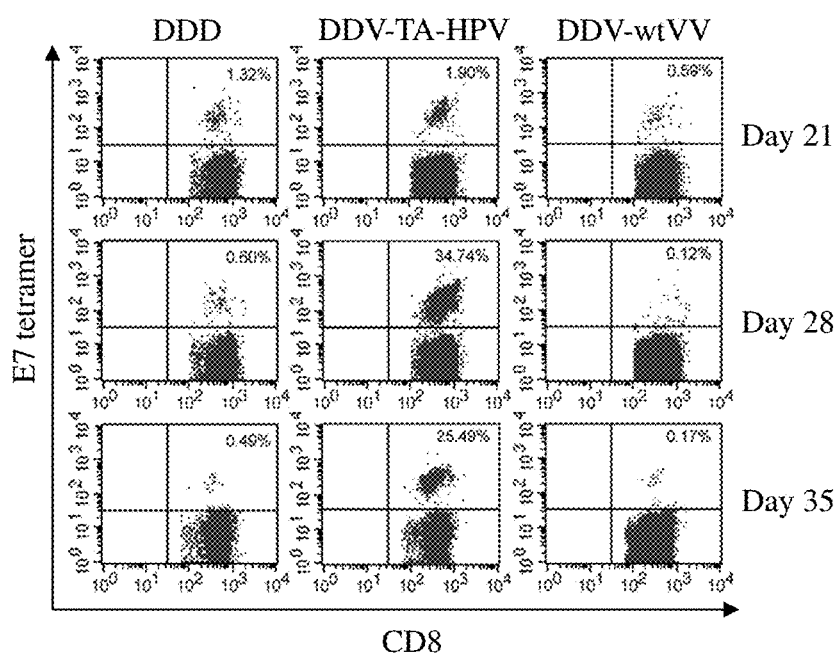
FIG. 1E shows representative flow cytometry analysis of E7 tetramer-stained PBMC taken on days 21, 28 or 35 day as shown in FIG. 1D and illustrating the effect of TA-HPV versus wild-type vaccinia virus administration on boosting the immune response to pNGVL4a-sig/E7(detox)/HSP70 DNA vaccine vaccination in naïve C57BL/6 mice, as described in EXAMPLE 1.
Figure 1F:
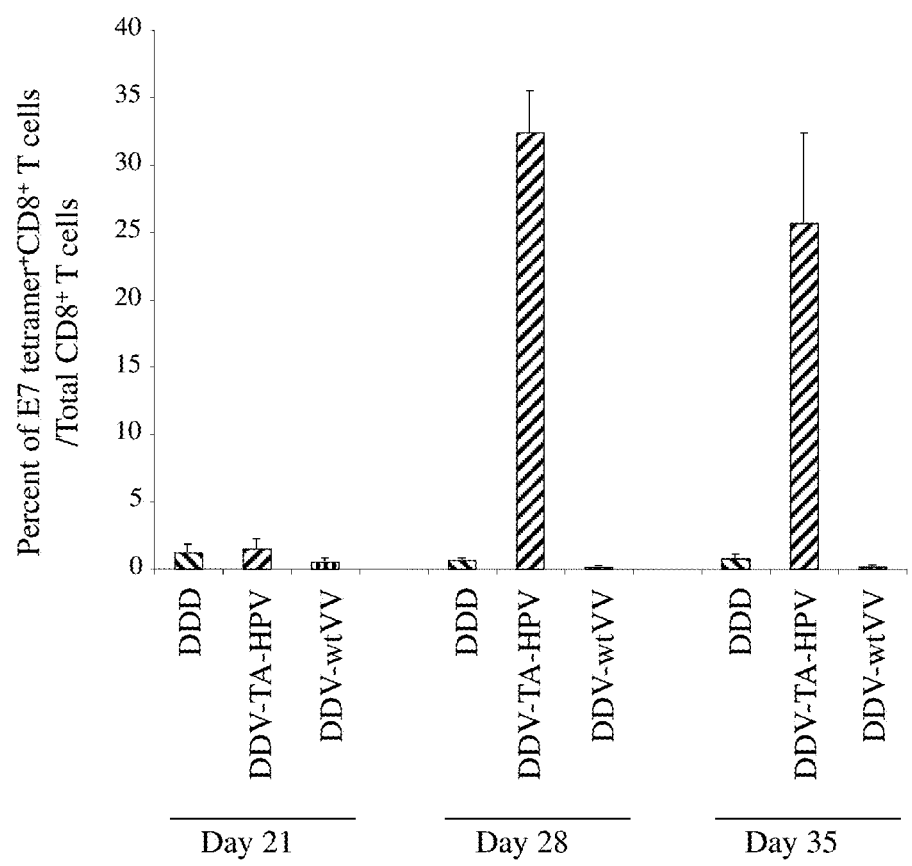
FIG. 1F is a summary of flow cytometry analysis of E7 tetramer-stained PBMC taken on days 21, 28 or 35 day as shown in FIG. 1D and illustrating the effect of TA-HPV versus wild-type vaccinia virus (wtVV) administration on boosting the immune response to pNGVL4a-sig/E7(detox)/HSP70 DNA vaccine vaccination in naïve C57BL/6 mice, as described in EXAMPLE 1.

In addition, the mice are administered with twice the pNGVL4a-sig/E7(detox)/HSP70 DNA vaccine vaccination and boosted with either the TA-HPV (DDV-TA-HPV) or wtVV (DDV-wtVV) via skin scarification (FIG. 1D) to determine whether the boosting effect observed from TA-HPV skin scarification is mediated by antigen-specific or non-specific immunity. As shown in FIGS. 1E and 1F, significant E7-specific CD8+ T cell responses are observed in the mice boosted with the TA-HPV, but not in the mice boosted with the wtVV.

Figure 1G:
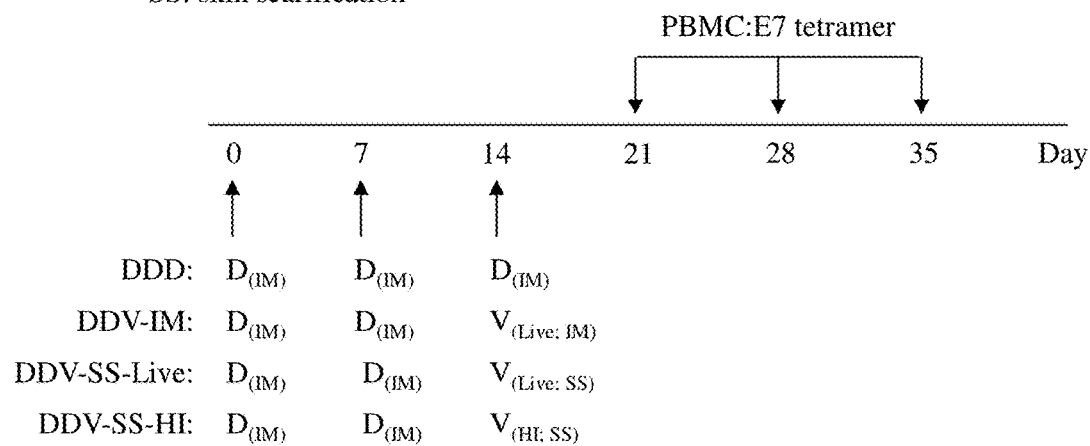
FIG. 1G shows live TA-HPV or heat-inactivated (HI) TA-HPV administration boosted pNGVL4a-sig/E7(detox)/HSP70 DNA vaccine vaccination in naïve C57BL/6 mice, as described in EXAMPLE 1.
Figure 1H:
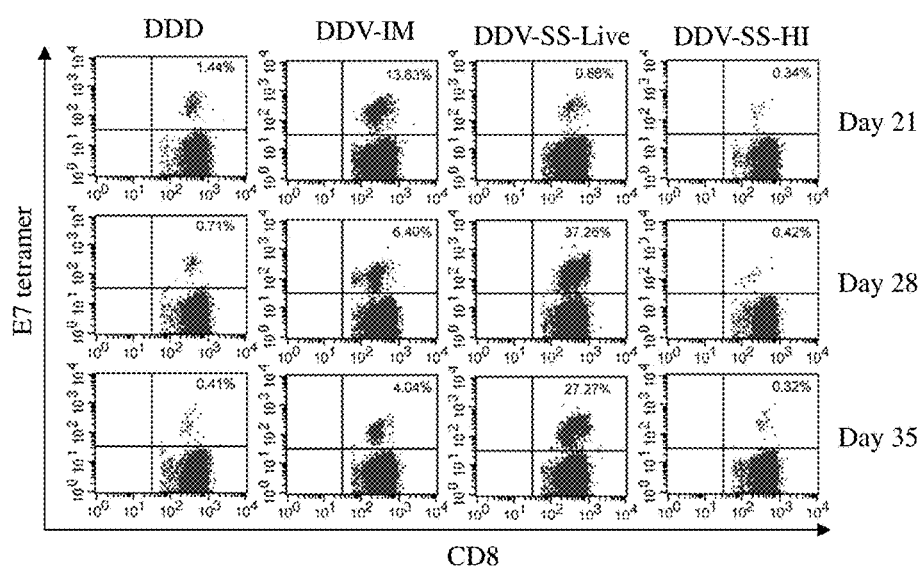
FIG. 1H shows representative flow cytometry analysis of E7-tetramer-stained PBMC taken on days 21, 28, or 35 day as shown in FIG. 1G and illustrating the effect of live TA-HPV versus heat-inactive TA-HPV administration on boosting the immune response to pNGVL4a-sig/E7(detox)/HSP70 DNA vaccine vaccination in naïve C57BL/6 mice, as described in EXAMPLE 1.
Figure 1I:
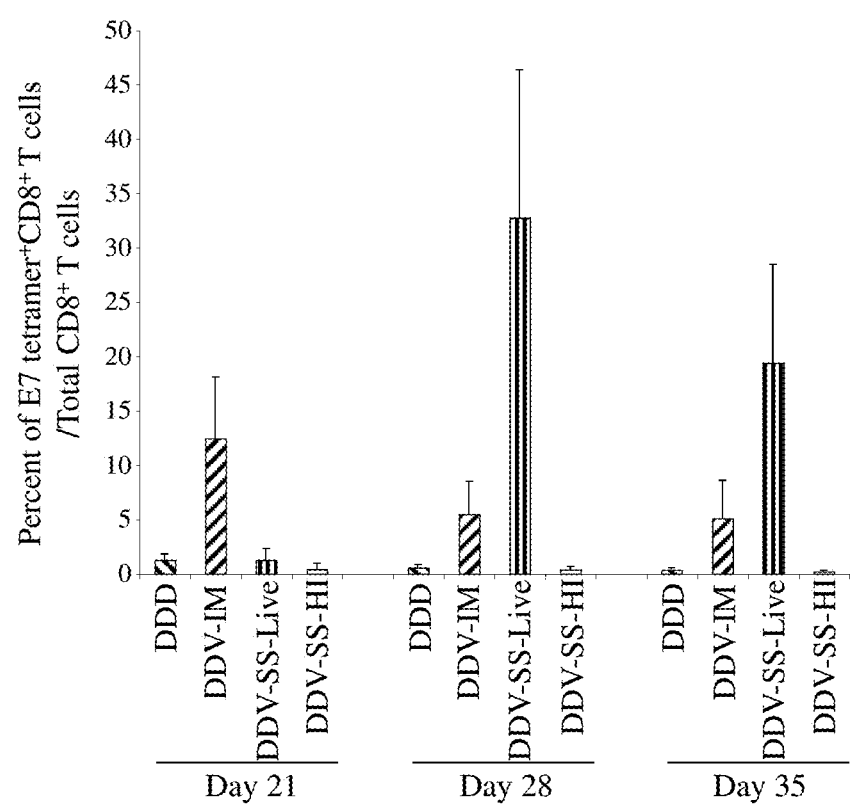
FIG. 1I is a summary of flow cytometry analysis of E7-tetramer-stained PBMC taken on days 21, 28, or 35 day as shown in FIG. 1G and illustrating the effect of live TA-HPV versus heat-inactive TA-HPV administration on boosting the immune response to pNGVL4a-sig/E7(detox)/HSP70 DNA vaccine vaccination in naïve C57BL/6 mice, as described in EXAMPLE 1.

Furthermore, the mice are administered with twice the pNGVL4a-sig/E7(detox)/HSP70 DNA vaccine vaccination and boosted with either the live TA-HPV via intramuscular injection (DDV-IM), live TA-HPV via skin scarification (DDV-SS-Live), or heat inactivated TA-HPV via skin scarification (DDV-SS-HI) (FIG. 1G) to determine whether the boosting effect observed from the TA-HPV skin scarification requires the biological activity of the vaccinia virus. As shown in FIGS. 1H and 1F, significant E7-specific CD8+ T cell responses are observed in the mice boosted with the live TA-HPV, but not in the mice boosted with the heat inactivated TA-HPV.

Figure 1J:
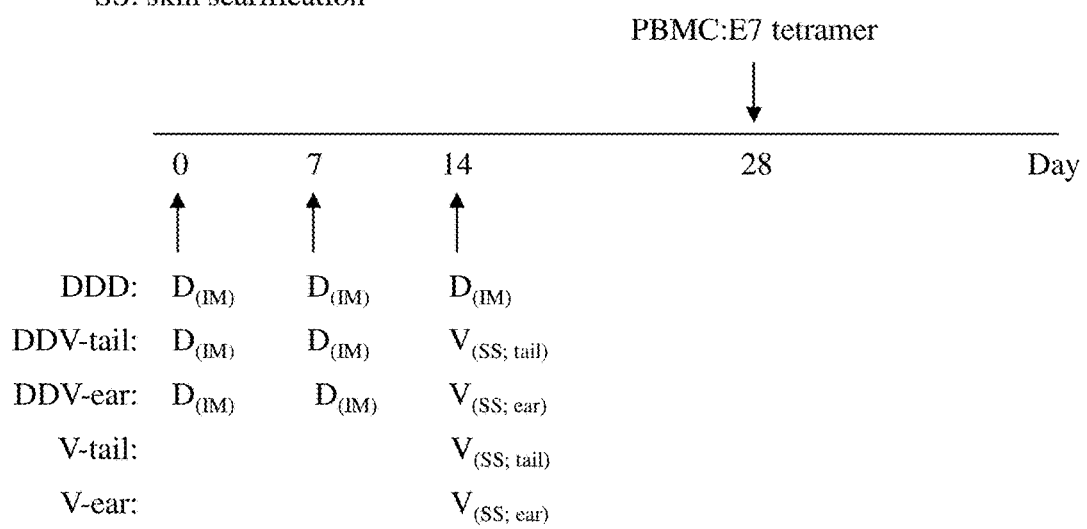
FIG. 1J shows ear or tail TA-HPV administration boosted pNGVL4a-sig/E7(detox)/HSP70 DNA vaccine vaccination in naïve C57BL/6 mice, as described in EXAMPLE 1.
Figure 1K:
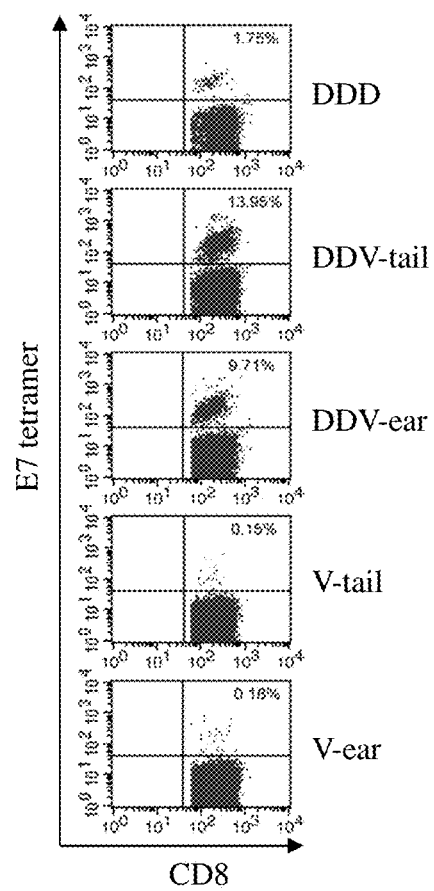
FIG. 1K shows representative flow cytometry analysis of E7-tetramer-stained PBMC taken on day 28 as shown in FIG. 1J and illustrating the effect of ear TA-HPV versus tail TA-HPV administration on boosting the immune response to pNGVL4a-sig/E7(detox)/HSP70 DNA vaccine vaccination in naïve C57BL/6 mice, as described in EXAMPLE 1.
Figure 1L:
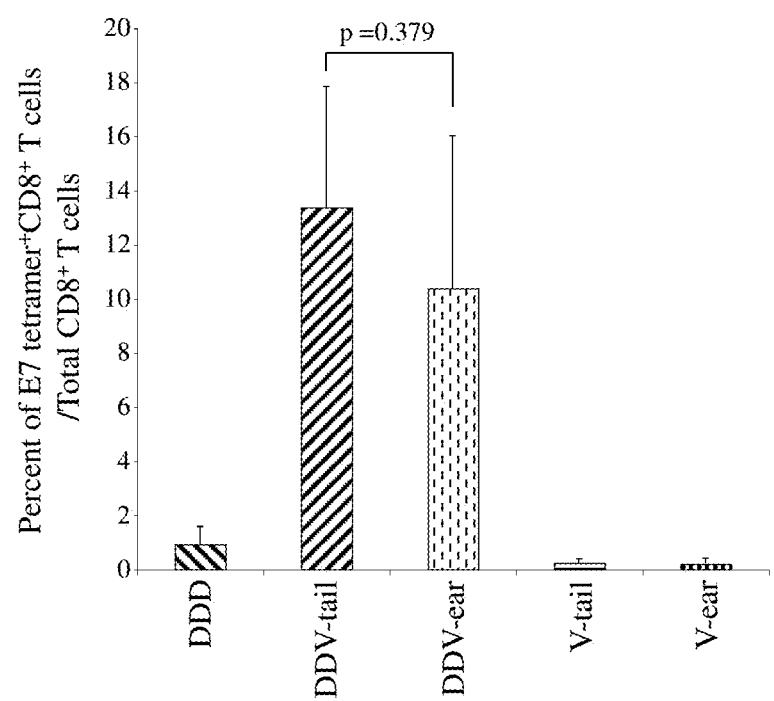
FIG. 1L is a summary of flow cytometry analysis of E7-tetramer-stained PBMC taken on day 28 as shown in FIG. 1J and illustrating the effect of ear TA-HPV versus tail TA-HPV administration on boosting the immune response to pNGVL4a-sig/E7(detox)/HSP70 DNA vaccine vaccination in naïve C57BL/6 mice, as described in EXAMPLE 1.

Likewise, the mice are vaccinated with three times of the pNGVL4a-sig/E7(detox)/HSP70 DNA vaccine vaccination (DDD) or twice the pNGVL4a-sig/E7(detox)/HSP70 DNA vaccine vaccination and boosted with the TA-HPV through skin scarification either at the base of the tail (DDV-tail) or the ear (DDV-ear) (FIG. 1J) to determine whether boosting effect observed from the TA-HPV skin scarification is dependent on the location of administration. As shown in FIGS. 1K and 1L, no significant differences are observed between the E7-specific CD8+ T cell responses elicited by mice boosted with the TA-HPV via tail skin scarification or via ear skin scarification.

Overall, these data suggest that administration of the live TA-HPV through skin scarification can enhance the HPV16 E7-specific CD8+ T cell responses in the pNGVL4a-sig/E7 (detox)/HSP70 DNA vaccine vaccinated mice.

Example 2

Figure 2A:
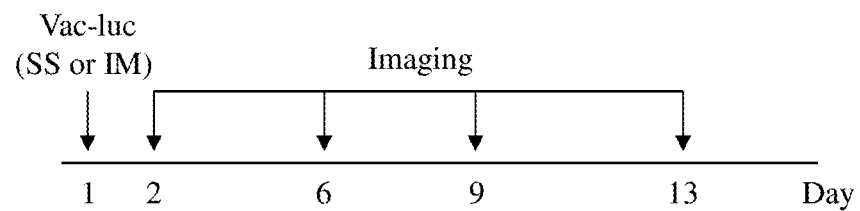
FIG. 2A shows luciferase expression experiments by vaccinia virus administration through either skin scarification or intramuscular injection in naïve C57BL/6 mice, as described in EXAMPLE 2.
Figure 2B:
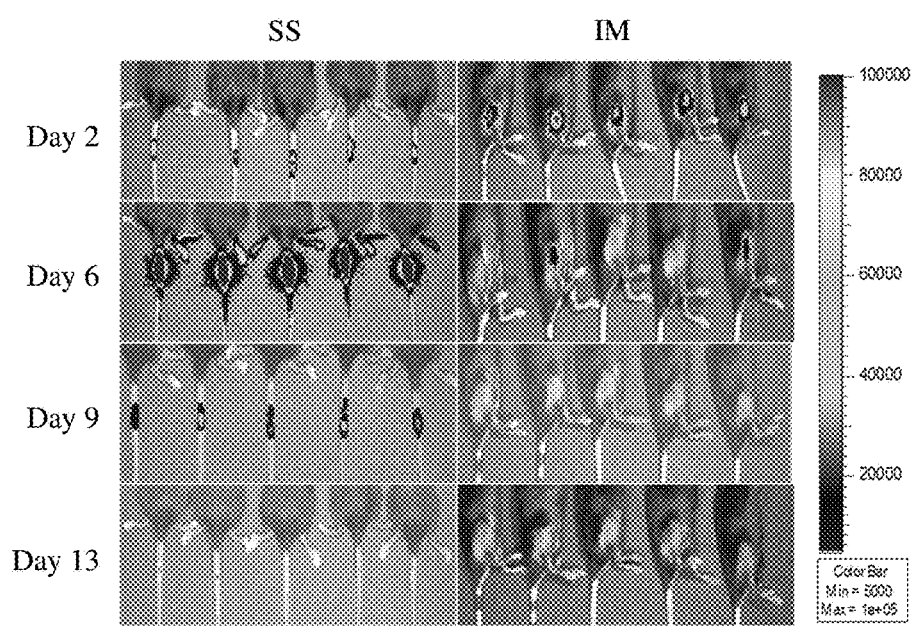
FIG. 2B shows representative luminescence images of luciferase expression experiments by luciferase recombinant vaccinia virus (Vac-luc) administration through either skin scarification or intramuscular injection in naïve C57BL/6 mice, as described in EXAMPLE 2.
Figure 2C:
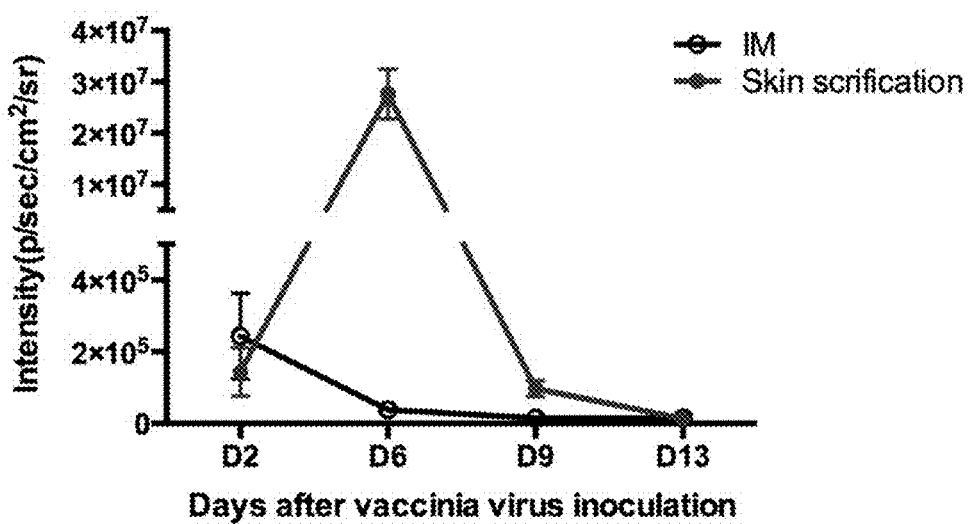
FIG. 2C is a summary of luminescence imaging data of luciferase expression experiments by luciferase recombinant vaccinia virus (Vac-luc) administration through either skin scarification or intramuscular injection in naïve C57BL/6 mice, as described in EXAMPLE 2.

To examine the potential mechanism that contributes to the observation in FIGS. 1A-1I, luciferase-expressing vaccinia virus is administered to the 5-8 week old female naïve C57BL/6 mice via IM injection or skin scarification on the tail. Luciferase expression is then monitored using luminescence imaging at indicated intervals as illustrated in FIG. 2A. As shown in FIGS. 2B-2C, the mice administered with the expressing luciferase vaccinia virus through skin scarification show a steady increase of luminescence signals from day 2 to day 6 before the signal starts to decrease. However, the mice administered with the expressing luciferase vaccinia virus through IM injection show a rapid decrease of the luminescence signals after the virus injection. The increases in luminescence intensity translate into an increase in an abundance of luciferase expressing cells around the administration site. Thus, the data suggest that the vaccinia virus unexpectedly experiences greater replication when the vaccinia virus is administered via skin scarification into the mice and amplifies and extends the expression of encoded protein antigens, resulting in greater immune responses. In other words, the mice administered vaccinia virus through skin scarification have greater luciferase intensity than mice vaccinated through IM injection.

Example 3

Figure 3A:
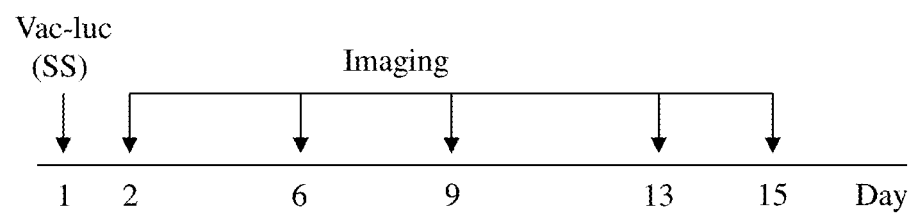
FIG. 3A shows dose response experiments of luciferase expression by luciferase recombinant vaccinia virus (Vac-luc) administration through either skin scarification or intramuscular injection in naïve C57BL/6 mice, as described in EXAMPLE 3.
Figure 3B:
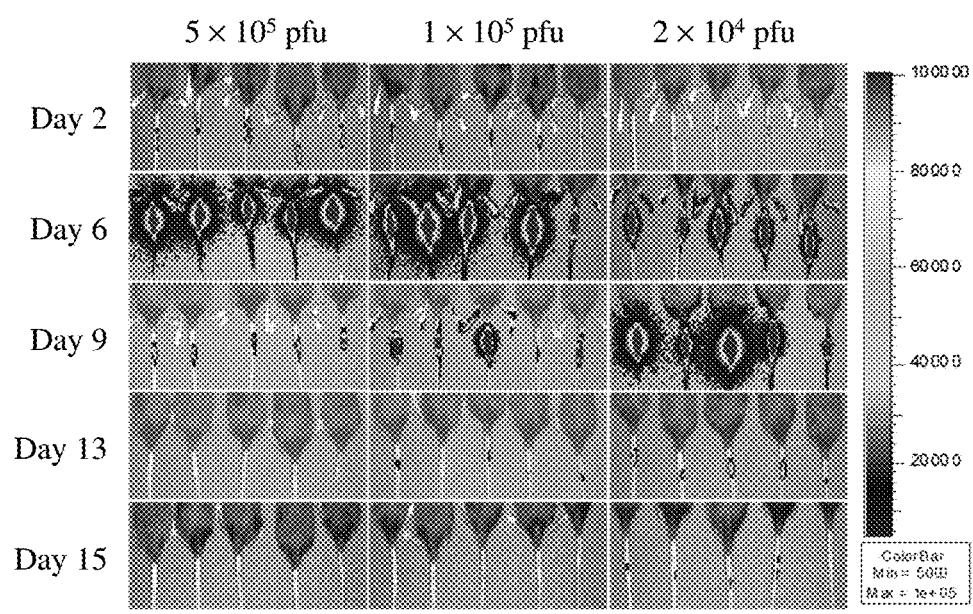
FIG. 3B shows representative luminescence images of dose response experiments of luciferase expression by luciferase recombinant vaccinia virus (Vac-luc) administration through either skin scarification or intramuscular injection in naïve C57BL/6 mice, as described in EXAMPLE 3.
Figure 3C:
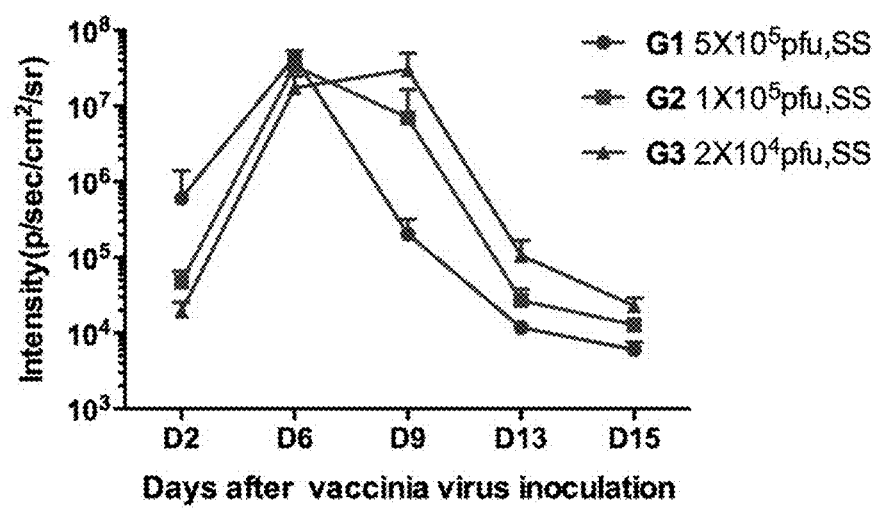
FIG. 3C is a summary of luminescence imaging data of dose response experiments of luciferase expression by luciferase recombinant vaccinia virus (Vac-luc) administration through either skin scarification or intramuscular injection in naïve C57BL/6 mice, as described in EXAMPLE 3.

To determine whether changes in administration dosage would influence the protein expression kinetics, the 5-8 week old female naïve mice are administered with varying doses of the expressing luciferase vaccinia virus ($5 \times 10^5$ pfu (G1), $1 \times 10^5$ pfu (G2), or $2 \times 10^4$ pfu (G3)) via skin scarification on the tail. The luciferase expression is then monitored for 15 days using the luminescence imaging at indicated intervals (FIG. 3A). As shown in FIGS. 3B-3C, skin scarification of luciferase encoded vaccinia virus at the three tested doses show similar luminescence signal kinetics, all reaching their peak luminescence intensity around 6 or 9 days after administration and decrease rapidly to almost background level on day 15. Importantly, there are no significant differences in the luminescence signal kinetics are observed between the groups with high ($5 \times 10^5$ pfu) or low ($2 \times 10^4$ pfu) dose of the expressing luciferase vaccinia virus. The experimental data suggest that administration of low dose ($2 \times 10^4$ pfu) of the expressing luciferase vaccinia virus through skin scarification is capable of generating comparable amount of antigens as the high dose.

Example 4

Figure 4A:
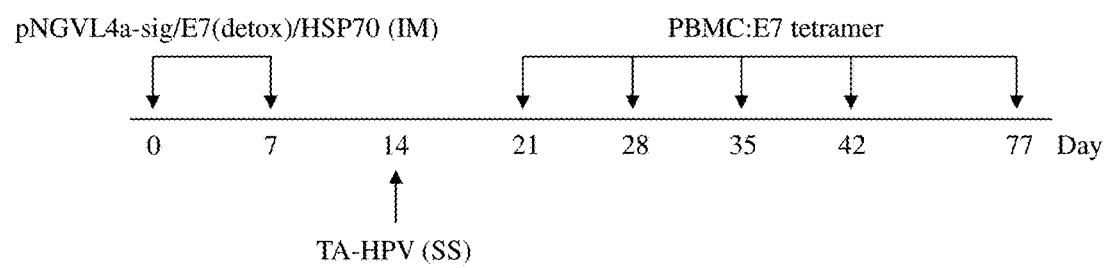
FIG. 4A shows TA-HPV administration with different doses boosted pNGVL4a-sig/E7(detox)/HSP70 DNA vaccine vaccination in naïve C57BL/6 mice, as described in EXAMPLE 4.
Figure 4B:
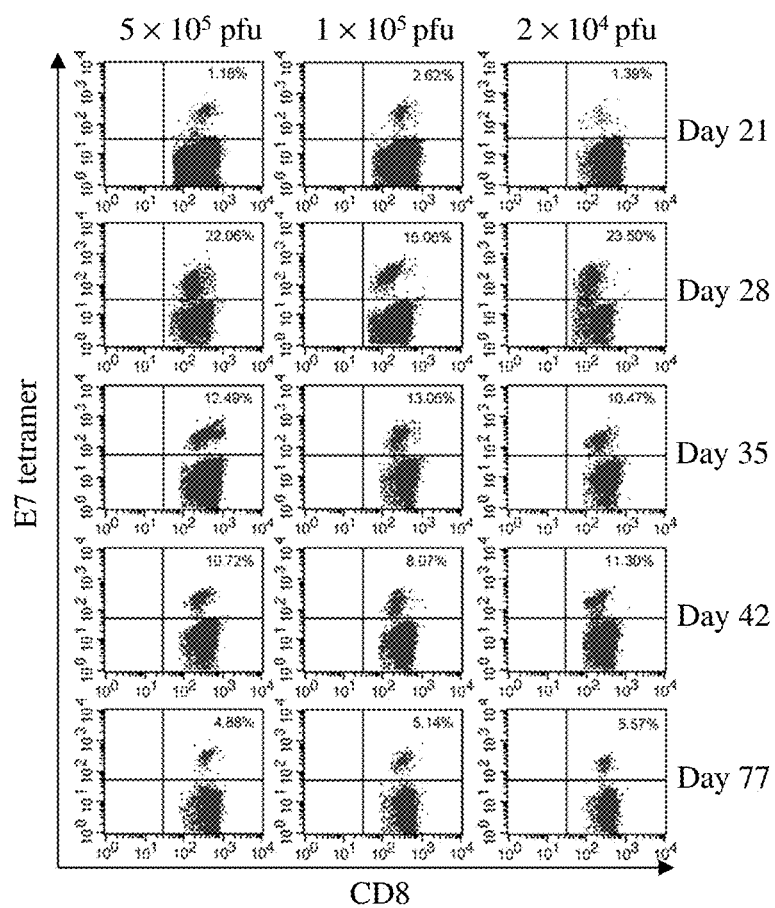
FIG. 4B shows representative flow cytometry images of E7 stained from PBMC taken from naïve C57BL/6 mice after pNGVL4a-sig/E7(detox)/HSP70 DNA vaccine vaccination twice and a single TA-HPV administration at different doses, as described in EXAMPLE 4.
Figure 4C:
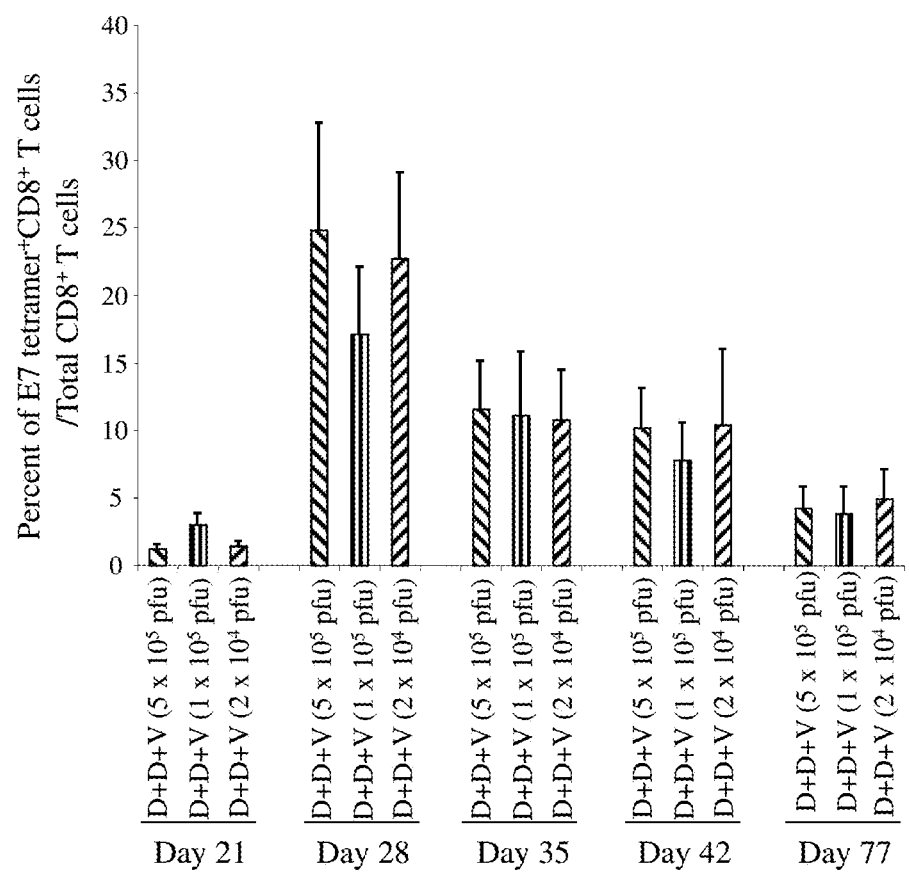
FIG. 4C is a summary of flow cytometry data of E7 stained from PBMC taken from naïve C57BL/6 mice after pNGVL4a-sig/E7(detox)/HSP70 DNA vaccine vaccination twice and a single TA-HPV administration at different doses, as described in EXAMPLE 4.

To test the antigen-specific immune responses, the 5-8 week old female naïve C57BL/6 mice are administered with IM injection of the pNGVL4a-sig/E7(detox)/HSP70 DNA vaccine on day 0 and day 7, followed by boosting with different doses of the TA-HPV ($5 \times 10^5$ pfu, $1 \times 10^5$ pfu, or $2 \times 10^4$ pfu) via skin scarification on day 14. PBMCs are prepared on days 21, 28, 35, 42 and 77, and stained with anti-mouse CD8 and HPV16 E7 tetramer, and then analyzed through flow cytometry (FIG. 4A). As shown in FIGS. 4B-4C, the resulted E7-specific CD8+ T cell responses elicited by the TA-HPV booster vaccination are comparable among the three tested doses of the TA-HPV. These data, together with the findings observed in FIGS. 3A-3C, suggest that the pNGVL4a-sig/E7(detox)/HSP70 DNA vaccine IM injection prime with the TA-HPV skin scarification boosting vaccination regimen is capable of eliciting potent HPV16 E7-specific CD8+ T cell response even at the lowest tested dose ($2 \times 10^4$ pfu).

Example 5

Figure 5A:
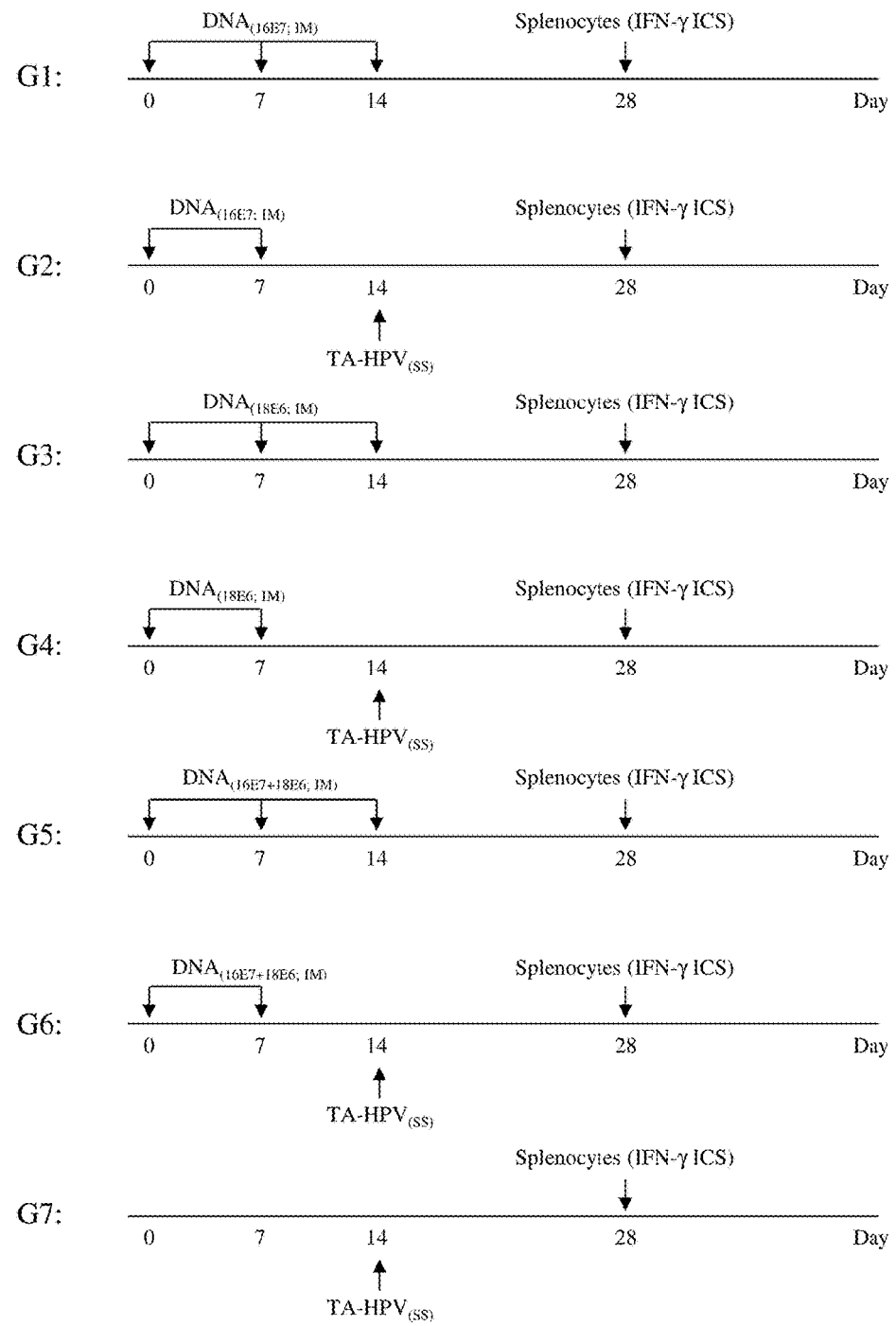
FIG. 5A shows TA-HPV administration boosted multiple DNA vaccines vaccination with various treatment regimens (G1 to G7) in naïve C57BL/6 mice and as described in EXAMPLE 5.
Figure 5B:
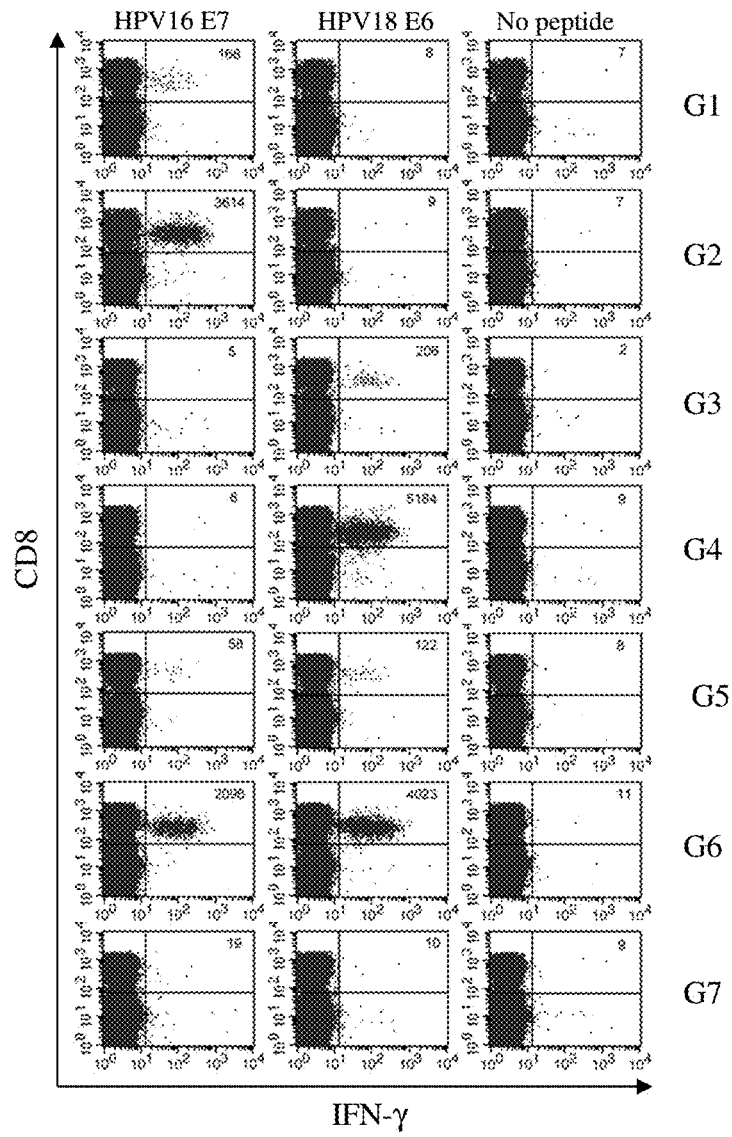
FIG. 5B shows representative flow cytometry analysis of TA-HPV administration boosted multiple DNA vaccines vaccination with various treatment regimens (G1 to G7) in naïve C57BL/6 mice and as described in EXAMPLE 5.
Figure 5C:
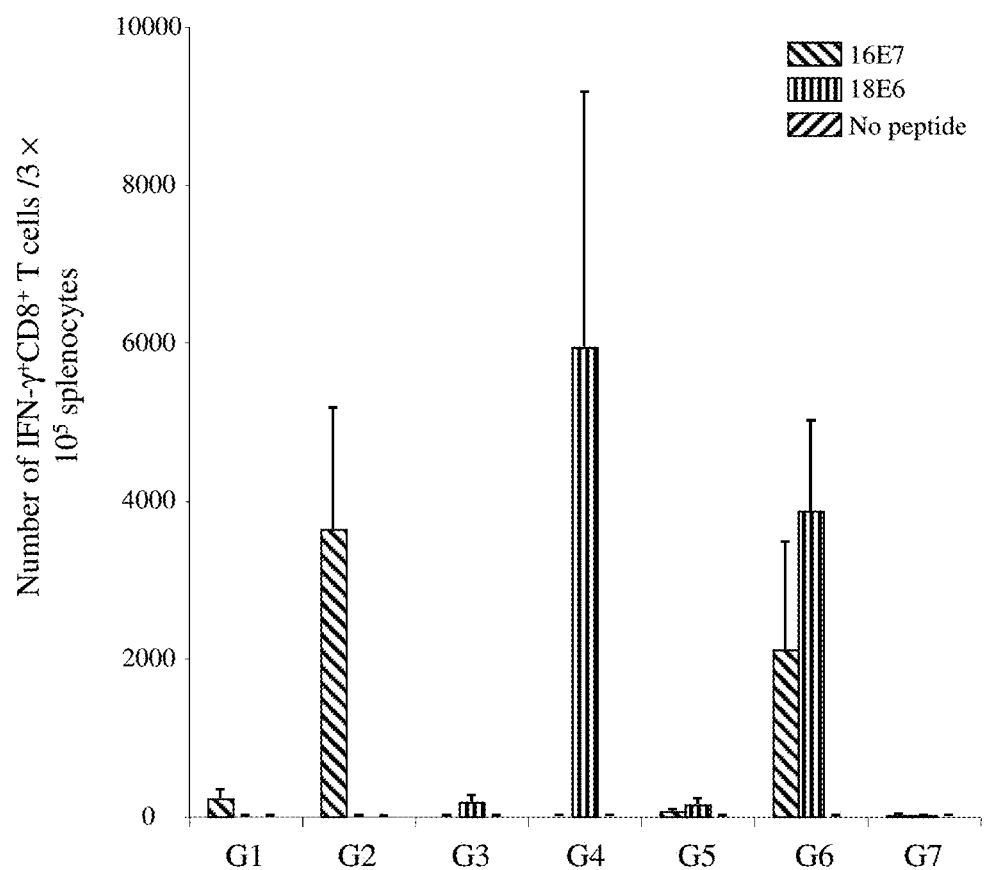
FIG. 5C is a summary of flow cytometry data of TA-HPV administration boosted multiple DNA vaccines vaccination with various treatment regimens (G1 to G7) in naïve C57BL/6 mice and as described in EXAMPLE 5.

Since the TA-HPV encodes four antigens comprising HPV type 16-E6, HPV type 16-E7, HPV type 18-E6 and HPV type 18-E7, the TA-HPV can potentially enhance the immune responses against multiple antigens simultaneous. To evaluate the ability of the TA-CIN to boost the immune response against multiple HPV antigens, the 5-8 week old female naïve C57BL/6 mice are vaccinated with a DNA vaccine encoding HPV type 16 E7 and/or HPV type 18 E6 via IM injection on day 0 and day 7, followed by the administration of the TA-HPV through skin scarification on day 14 (FIG. 5A). On day 28, splenocytes are obtained from different groups of the mice, and stimulated with either HPV16 E7aa49-57 peptide or HPV18 E6aa67-75 peptide, and further analyzed using flow cytometry. As shown in FIGS. 5B-5C, the TA-HPV vaccination through skin scarification significantly enhances the immune responses elicited by the priming of DNA encoding a single antigen (either HPV type 16 E7 or HPV type 18 E6) in the vaccinated mice. Furthermore, the mice administered with the combinational the DNA vaccines vaccination containing both HPV type 16 E7 and HPV type 18 E6 antigens followed by boosting with the TA-HPV skin scarification induced both enhanced HPV16 E7 and HPV18 E6 specific CD8+ T cell responses. These results show that the TA-HPV administered via skin scarification is able to enhance the antigen-specific CD8+ T cell immune responses primed by the DNA vaccines vaccination against multiple antigens simultaneously.

Example 6

Figure 6A:
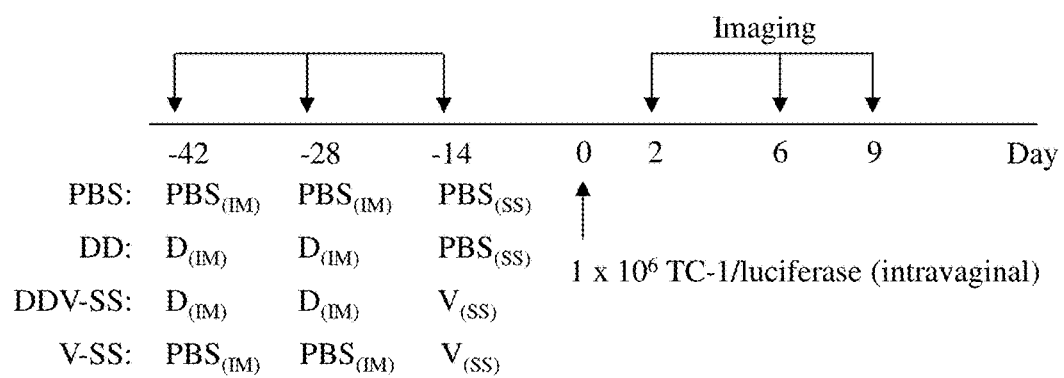
FIG. 6A shows an experiment testing pNGVL4a-sig/E7(detox)/HSP70 DNA vaccine vaccination alone, TA-HPV administration boosted pNGVL4a-sig/E7(detox)/HSP70 DNA vaccine vaccination, or TA-HPV administration alone for protection of C57BL/6 mice against a lethal cervicovaginal challenge with luciferase-expressing TC-1 tumor cells, as described in EXAMPLE 6.
Figure 6B:
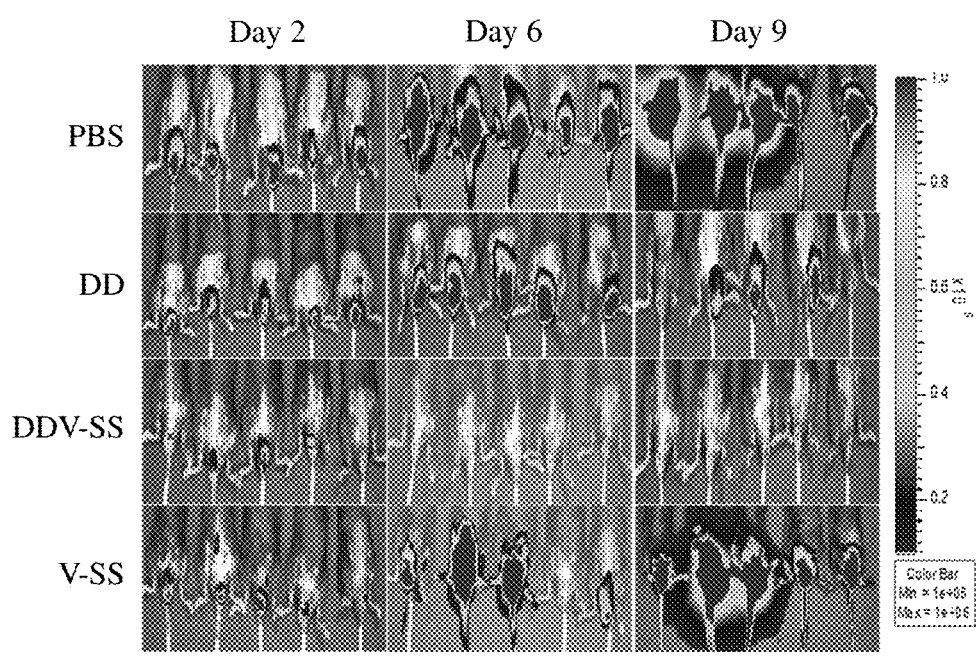
FIG. 6B shows representative luminescence images of C57BL/6 mice that had received pNGVL4a-sig/E7(detox)/HSP70 DNA vaccine vaccination alone, TA-HPV administration boosted pNGVL4a-sig/E7(detox)/HSP70 DNA vaccine vaccination, or TA-HPV administration alone and then a lethal cervicovaginal challenge with luciferase-expressing TC-1 tumor cells, as described in EXAMPLE 6.
Figure 6C:
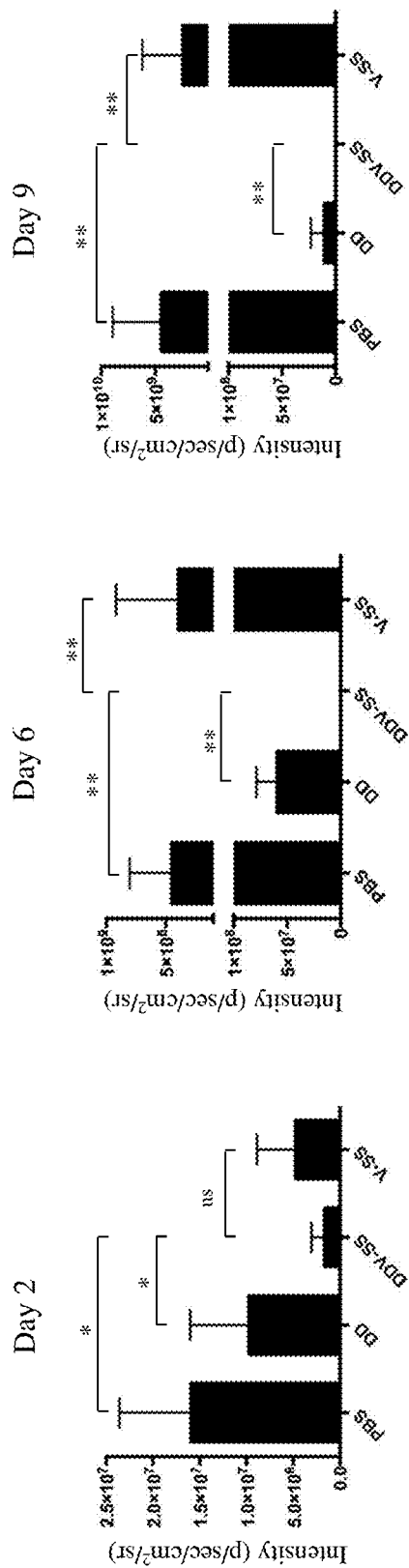
FIG. 6C is a summary of luminescence measurement data from C57BL/6 mice that had received pNGVL4a-sig/E7(detox)/HSP70 DNA vaccine vaccination alone, TA-HPV administration boosted pNGVL4a-sig/E7(detox)/HSP70 DNA vaccine vaccination, or TA-HPV administration alone and then a lethal cervicovaginal challenge with luciferase-expressing TC-1 tumor cells, as described in EXAMPLE 6.

To examine whether the immunogenicity of the vaccine regimen translates into potent antitumor effects against HPV+ cervical tumors, the 5-8 week old female naïve C57BL/6 mice are treated with various treatment regimens comprising 1) PBS control injections; 2) two pNGVL4a-sig/E7(detox)/HSP70 DNA vaccine IM injections; 3) two pNGVL4a-sig/E7(detox)/HSP70 DNA vaccine IM injections followed by one TA-HPV skin scarification; or 4) one TA-HPV skin scarification (FIG. 6A). Two weeks after the last treatment administration, the mice are challenged with $1 \times 10^6$ TC-1/luciferase tumor cells intravaginally, and the subsequent luminescence intensity is measured as a representation of tumor growth. As shown in FIGS. 6B-6C, the mice treated with the PBS only or the TA-HPV skin scarification only do not generate protective immunity against TC-1 tumor challenge. The luminescence signals in the mice administered PBS only or TA-HPV skin scarification only increase exponentially during the examined time points. Furthermore, the mice treated with pNGVL4a-sig/E7(detox)/HSP70 only generate some degree of protective immunity against TC-1 tumor challenge. The mice administered with the pNGVL4a-sig/E7(detox)/HSP70 injections followed by TA-HPV skin scarification generate the most potent protective immune response against tumor challenge as the luminescence signals decreased to back ground level within 6 days after tumor challenge. These results show that the TA-HPV skin scarification boost leads to enhanced anti-tumor immunity following priming with the pNGVL4a-sig/E7(detox)/HSP70 DNA vaccine vaccination.

Example 7

Figure 7A:
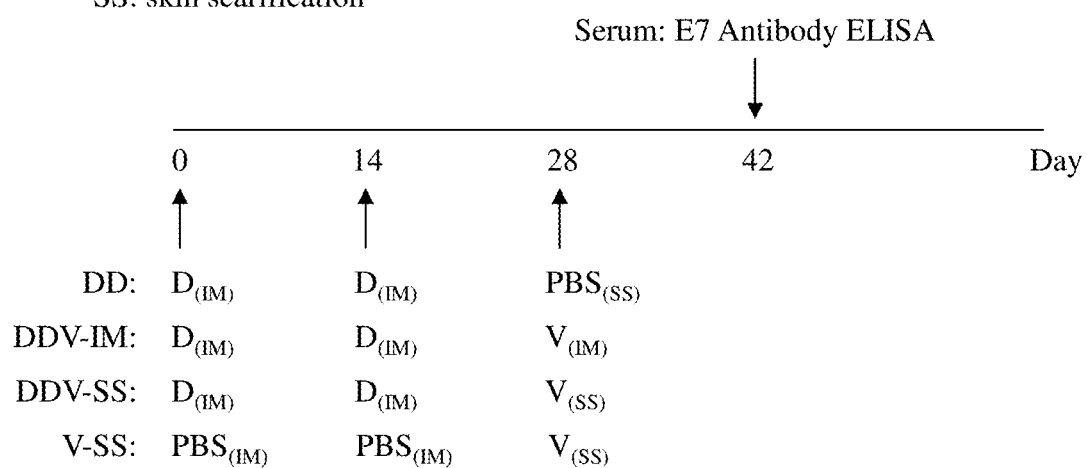
FIG. 7A shows an experiment testing pNGVL4a-sig/E7(detox)/HSP70 DNA vaccine vaccination alone, intramuscular TA-HPV administration boosted pNGVL4a-sig/E7(detox)/HSP70 DNA vaccine vaccination, skin scarification TA-HPV administration boosted pNGVL4a-sig/E7(detox)/HSP70 DNA vaccine vaccination or TA-HPV administration alone for generation of E7-specific humoral response by C57BL/6 mice, as described in EXAMPLE 7.
Figure 7B:
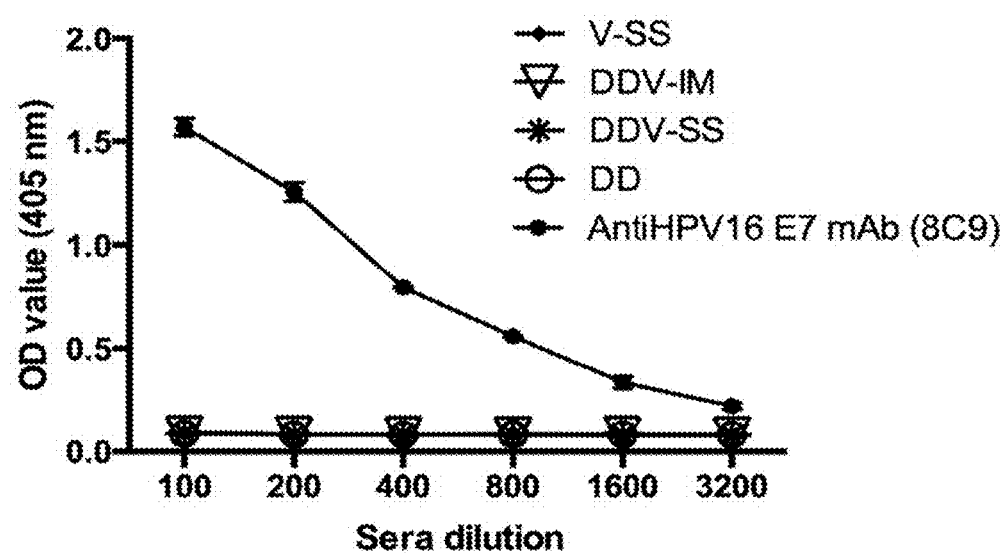
FIG. 7B is a summary of HPV16 E7 ELISA data measuring HPV16 E7 antibody response in sera taken from C57BL/6 mice 2 week after vaccination with 1) pNGVL4a-sig/E7(detox)/HSP70 DNA vaccine vaccination twice, 2) TA-HPV administration via tail skin scarification (base of tail) after two pNGVL4a-sig/E7(detox)/HSP70 DNA vaccine vaccinations, 3) TA-HPV administration intramuscularly after two pNGVL4a-sig/E7(detox)/HSP70 DNA vaccine vaccinations, or 4) TA-HPV administration alone via tail skin scarification (base of tail), as described in EXAMPLE 7.

To examine whether the vaccine regimen generates any E7-specific humoral response, 5-8 week old female naïve C57BL/6 mice are treated with various treatment regimens comprising 1) two pNGVL4a-sig/E7(detox)/HSP70 DNA vaccine IM injections; 2) two pNGVL4a-sig/E7(detox)/HSP70 DNA vaccine IM injections followed by one TA-HPV injection IM; 3) two pNGVL4a-sig/E7(detox)/HSP70 DNA vaccine IM injections followed by one TA-HPV skin scarification; and 4) one TA-HPV skin scarification (FIG. 7A). Two weeks after the last treatment administration, serum of all treatment regimens mice are harvested and the antibody titer for antibody against HPV16-E7 proteins is examined using ELISA. The monoclonal antibody 8C9 is used as a positive control for the HPV16 E7 ELISA. As shown in FIG. 7B, the mice from all treatment groups showed a similar level of E7-specific antibody titer at background level, suggesting the vaccination regimen predominantly elicit T-cell mediated immunity and not B-cell mediated humoral immunity.

Example 8

Figure 8A:
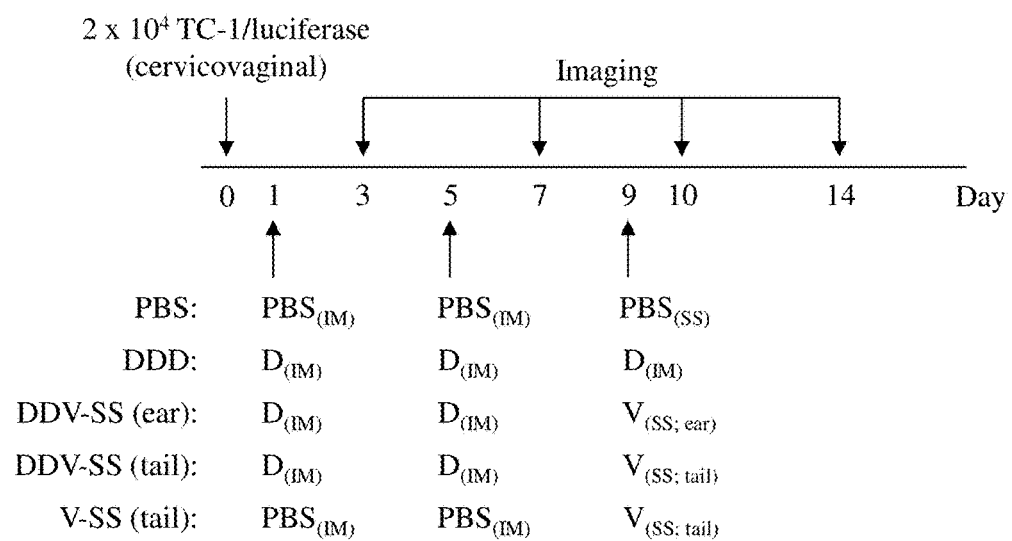
FIG. 8A shows an experiment to test the impact of pNGVL4a-sig/E7(detox)/HSP70 DNA vaccine vaccination three times, TA-HPV administration via ear skin scarification after two pNGVL4a-sig/E7(detox)/HSP70 DNA vaccine vaccinations, TA-HPV administration via tail skin scarification after two pNGVL4a-sig/E7(detox)/HSP70 DNA vaccine vaccinations, or TA-HPV administration alone via tail skin scarification against luciferase-expressing cervicovaginal TC-1 tumors established in C57BL/6 mice, as described in EXAMPLE 8.
Figure 8B:
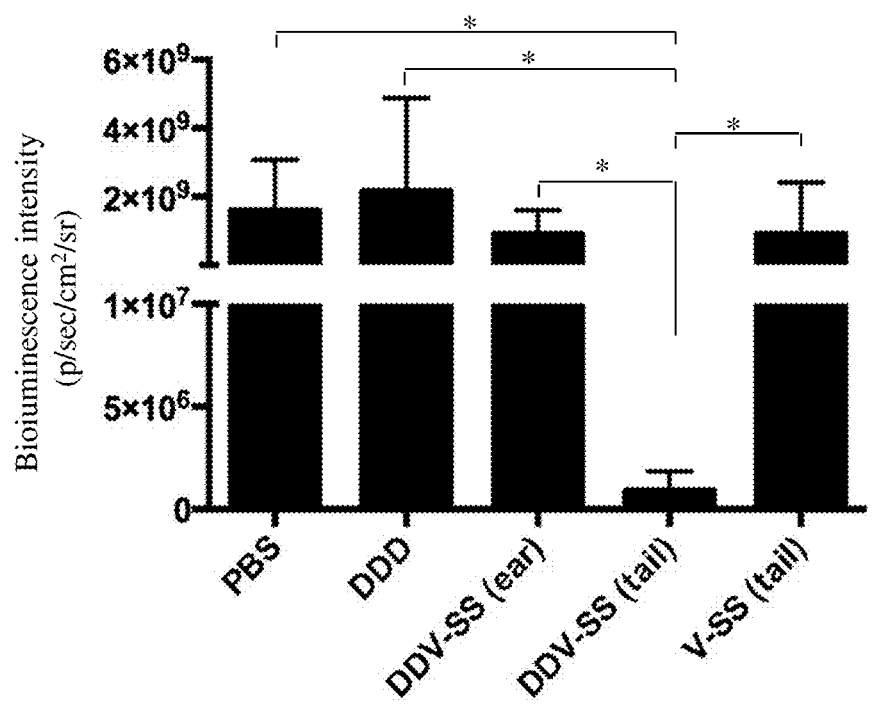
FIG. 8B is a summary of luminescence imaging data from an experiment to test the impact of pNGVL4a-sig/E7(detox)/HSP70 DNA vaccine vaccination three times, TA-HPV administration via ear skin scarification after two pNGVL4a-sig/E7(detox)/HSP70 DNA vaccine vaccinations, TA-HPV administration via tail skin scarification after two pNGVL4a-sig/E7(detox)/HSP70 DNA vaccine vaccinations, or TA-HPV administration alone via tail skin scarification against luciferase-expressing cervicovaginal TC-1 tumors established in groups of C57BL/6 mice, as described in EXAMPLE 8.
Figure 8C:
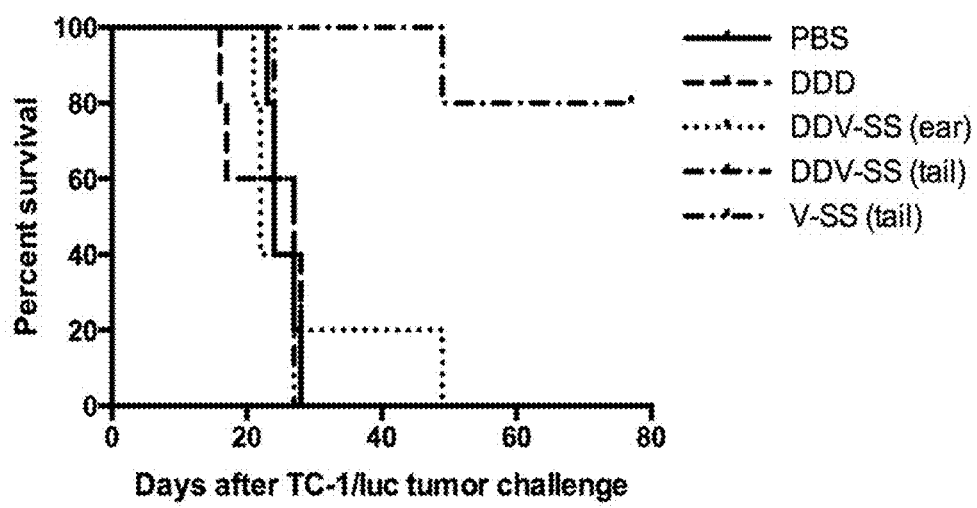
FIG. 8C is a Kaplan-Meier survival analysis from an experiment to test the impact of pNGVL4a-sig/E7(detox)/HSP70 DNA vaccine vaccination three times, TA-HPV administration via ear skin scarification after two pNGVL4a-sig/E7(detox)/HSP70 DNA vaccine vaccinations, TA-HPV administration via tail skin scarification after two pNGVL4a-sig/E7(detox)/HSP70 DNA vaccine vaccinations, or TA-HPV administration alone via tail skin scarification against luciferase-expressing cervicovaginal TC-1 tumors established in groups of C57BL/6 mice, as described in EXAMPLE 8.

To evaluate the therapeutic efficacy of the proposed prime boost vaccination regimen against pre-existing tumor, the 5-8 week old female naïve C57BL/6 mice are challenged with $2 \times 10^4$ TC-1/luciferase tumor cells intravaginally and then treated with various treatment regimens at the first day after tumor challenge, comprising 1) PBS control (PBS); 2) three times IM pNGVL4a-sig/E7(detox)/HSP70 DNA vaccine vaccination in 2 day intervals (DDD); 3) pNGVL4a-sig/E7(detox)/HSP70 DNA vaccine is administered twice IM with a 2 day interval followed by the TA-HPV via skin scarification on the ear 2 days after the last DNA vaccine vaccination (DDV-SS (ear)); 4) pNGVL4a-sig/E7(detox)/HSP70 DNA vaccine is administered twice IM with a 2 day interval followed by the TA-HPV via skin scarification on the tail 2 days after the last DNA vaccine vaccination (DDV-SS (tail)); and 5) the TA-HPV via skin scarification on the tail at the ninth day after the tumor cells challenge (V-SS (tail)) (FIG. 8A). Luminescence imaging is performed starting at the third day after the tumor cells challenge and continued in 4 day intervals. As shown in FIG. 8B, at the $14^{th}$ day after the tumor cells challenge, the mice treated with DDV-SS (tail) show a significantly lower luminescence intensity compared to the mice in all other groups. Furthermore, 8°% of mice administered with DDV-SS (tail) survive more than 80 days after the tumor cells challenge. For all other treatment regimens the mice died in less than 50 days after the tumor cells challenge (FIG. 8C).

In the present disclosure, we show that administration of the TA-HPV through skin scarification is able to produce a more potent HPV16 E7-specific CD8+ T cell response than IM injection. Therapeutic HPV DNA vaccines and the IA-HPV have been successfully used as a combinational therapeutic treatment strategy in preclinical and clinical studies. However, the administration of the TA-HPV via skin scarification in. DNA prime, the TA-HPV boost regimen has not been previously explored. The present disclosure warrants future clinical translation of the heterologous pNGVL4a-sig/E7(detox)/HSP70 DNA vaccine prime and the TA-HPV skin scarification boost vaccination regimen. Further it is shown that administration of TA-HPV skin scarification at a site that is adjacent to the site infected with papillomavirus and shares draining lymph nodes with the site carrying the HPV infection produces a more beneficial therapeutic response.

While the present disclosure has been presented in accordance with several preferred and practical embodiments thereof, it is recognized that departures from the instant disclosure are fully contemplated within the spirit and scope of the invention.

The examples shown and described above are only examples. Many details are often found in the art. Therefore, many such details are neither shown nor described. Even though numerous characteristics and advantages of the present technology have been set forth in the foregoing description, together with details of the structure and function of the present disclosure, the disclosure is illustrative only, and changes may be made in the detail, and including the full extent established by the broad general meaning of the terms used in the claims. It will therefore be appreciated that the examples described above may be modified within the scope of the claims.

What is claimed is:

1. A combination therapy comprising:
   a DNA vaccine, selected from a DNA expression vector-encoding CRT fusion protein with the CRT being fused in frame to an HPV E6 and/or E7 coding region, a pcDNA3-CRT/HPV16E7 DNA vaccine, a pcDNA3-CRT/HPV18E6 DNA vaccine, a pNGVL4a-CRT/HPV16E7(detox) DNA vaccine, a pNGVL4a-CRT/HPV18E6 DNA vaccine, a pNGVL4a-CRT/E6E7L2 DNA vaccine or a pNGVL4a-sig/E7(detox)/HSP70 DNA vaccine; and
   a recombinant vaccinia virus expressing E6 and E7 of human papillomavirus (HPV) types 16 and 18 and formulated to be administered to a site that shares draining lymph nodes with a site having HPV infection via skin scarification,
   wherein the combination therapy is used in a heterologous prime-boost regimen to enhance a subject's immune responses against HPV associated diseases, and the site of administration of the recombinant vaccinia virus does not include a deltoid region of an arm of the subject.

2. The combination therapy of claim 1, wherein a dosages ranging of the DNA vaccine is from 1 microgram per subject to 20 milligram per subject.

3. The combination therapy of claim 1, wherein the recombinant vaccinia virus is a TA-HPV recombinant vaccinia virus.

4. The combination therapy of claim 1, wherein a dosages ranging of the recombinant vaccinia virus is from $1 \times 10^4$ pfu to $2 \times 10^8$ pfu.

5. The combination therapy of claim 1, wherein the HPV associated diseases comprise diseases associated with HPV types 6, 11, 16, 18, 31, 33, 35, 39, 45, 51, 52, 56, 58, 59, 66 or 68.

6. The combination therapy of claim 1, wherein the HPV-associated diseases comprise warts, papilloma, intra-epithelial neoplasia, penile cancer, vaginal cancer, vulva cancer, anal cancer, oropharyngeal cancer, non-melanoma skin cancer, conjunctival cancer or cervical cancer.

7. The combination therapy of claim 1, wherein the subject comprises a human, or other mammals.

8. An administration method of a combination therapy comprising administering to a subject a preferable amount of the combination therapy comprising a DNA vaccine and a recombinant vaccinia virus expressing E6 and E7 of human papillomavirus (HPV) types 16 and 18,
   wherein the DNA vaccine is selected from a DNA expression vector-encoding CRT fusion protein with the CRT being fused in frame to an HPV E6 and/or E7 coding region, a pcDNA3-CRT/HPV16E7 DNA vaccine, a pcDNA3-CRT/HPV18E6 DNA vaccine, a pNGVL4a-CRT/HPV16E7(detox) DNA vaccine, a pNGVL4a-CRT/HPV18E6 DNA vaccine, a pNGVL4a-CRT/E6E7L2 DNA vaccine or a pNGVL4a-sig/E7(detox)/HSP70 DNA vaccine,
   the recombinant vaccinia virus is administered to a site that shares draining lymph nodes with a site having HPV infection via skin scarification,
   the combination therapy is used in a heterologous prime-boost regimen to enhance a subject's immune responses against HPV associated diseases, and
   the site of administration of the recombinant vaccinia virus does not include a deltoid region of an arm of the subject.

9. The administration method of claim 8, wherein the DNA vaccine is administered to the subject through intravenous, subcutaneous, intraperitoneal, intramuscular, intradermal mucosal injection or intralesional injection.

10. The administration method of claim 8, wherein a dosages ranging of the DNA vaccine is from 1 microgram per subject to 20 milligram per subject.

11. The administration method of claim 8, wherein the recombinant vaccinia virus is a TA-HPV recombinant vaccinia virus.

12. The administration method of claim 8, wherein a dosages ranging of the recombinant vaccinia virus is from $1 \times 10^4$ pfu to $2 \times 10^8$ pfu.

13. The administration method of claim 8, wherein the subject comprises a human, or other mammals.

14. The administration method of claim 8, wherein the HPV associated diseases comprises diseases associated with HPV types 6, 11, 16, 18, 31, 33, 35, 39, 45, 51, 52, 56, 58, 59, 66 or 68.

15. The administration method of claim 8, wherein the HPV-associated diseases comprise warts, papilloma, penile cancer, vaginal cancer, vulva cancer, anal cancer, oropharyngeal cancer or cervical cancer.

16. The administration method of claim 8, wherein the recombinant vaccinia virus is administered on a buttock or on a thigh of the subject to treat anogenital HPV diseases.

17. The administration method of claim 8, wherein the recombinant vaccinia virus is administered on a non-deltoid region of the arm of the subject to treat head and neck-related HPV diseases.

18. An administration method of a combination therapy comprising a DNA vaccine and a recombinant vaccinia virus, comprising steps of:
    1) administering the DNA vaccine to a subject; and
    2) administering the recombinant vaccinia virus to the subject,
    wherein the DNA vaccine is selected from a DNA expression vector-encoding CRT fusion protein with the CRT being fused in frame to an HPV E6 and/or E7 coding region, a pcDNA3-CRT/HPV16E7 DNA vaccine, a pcDNA3-CRT/HPV18E6 DNA vaccine, a pNGVL4a-CRT/HPV16E7(detox) DNA vaccine, a pNGVL4a-CRT/HPV18E6 DNA vaccine, a pNGVL4a-CRT/E6E7L2 DNA vaccine or a pNGVL4a-sig/E7(detox)/HSP70 DNA vaccine,
    the recombinant vaccinia virus expresses E6 and E7 of human papillomavirus (HPV) types 16 and 18, the recombinant vaccinia virus is administered to a site that shares draining lymph nodes with a site having HPV infection via skin scarification,
    the combination therapy is used in a heterologous prime-boost regimen to induce or enhance a therapeutic response, and
    the site of administration of the recombinant vaccinia virus does not include a deltoid region of an arm of the subject.

19. The administration method of claim 18, wherein the DNA vaccine is administered to the subject through intravenous, subcutaneous, intraperitoneal, intramuscular, intradermal mucosal injection or intralesional injection.

20. The administration method of claim 18, wherein the recombinant vaccinia virus is a TA-HPV recombinant vaccinia virus.

* * * * *

SEQUENCE LISTING

```
<160> NUMBER OF SEQ ID NOS: 10

<210> SEQ ID NO 1
<211> LENGTH: 1257
<212> TYPE: DNA
<213> ORGANISM: Homo sapiens

<400> SEQUENCE: 1
atgctgctcc ctgtgccgct gctgctcggc ctgctcggcc tggccgccgc cgagcccgtc      60
gtctacttca aggagcagtt tctggacgga gatgggtgga ccgagcgctg gatcgaatcc     120
aaacacaagt ccgattttgg caaattcgtc ctcagttcgg gcaagttcta cggcgatcag     180
gagaaagata aagggctgca gaccagccag gacgcccgct tctacgccct gtcggcccga     240
ttcgagccgt tcagcaacaa gggccagcca ctggtggtgc agttcaccgt gaaacacgag     300
cagaacattg actgcggggg cggctacgtg aagctgtttc cggccggcct ggaccagaag     360
gacatgcacg gggactctga gtacaacatc atgtttggtc ctgacatctg tggccccggc     420
accaagaagg ttcacgtcat cttcaactac aagggcaaga acgtgctgat caacaaggac     480
atccgttgca aggacgacga gttcacacac ctgtacacgc tgatcgtgcg gccggacaac     540
acgtatgagg tgaagattga caacagccag gtggagtcgg gctccctgga ggatgactgg     600
gacttcctac cccccaagaa gataaaggac ccagatgcct cgaagcctga agactgggac     660
gagcgggcca agatcgacga ccccacggac tccaagcccg aggactggga caagcccgag     720
cacatccccg acccggacgc gaagaagccc gaagactggg acgaagaaat ggacggagag     780
tgggagccgc cggtgattca gaaccccgag tacaagggtg agtggaagcc gcggcagatc     840
gacaaccccg attacaaagg cacctggatc cacccgaaa tcgacaaccc cgagtactcg     900
cccgacgcta acatctatgc ctacgacagc tttgccgtgc tgggcttgga cctctggcag     960
gtcaagtcgg gcaccatctt cgacaacttc ctcatcacca cgatgaggc gtacgcagag    1020 gagtttggca acgagacgtg gggcgtcacc aagacggccg agaagcagat gaaagacaag    1080
caggacgagg agcagcggct gaaggaggag gaggaggaga gaagcggaa ggaggaggag    1140 gaggccgagg aggacgagga ggacaaggac gacaaggagg acgaggatga ggacgaggag    1200
gacaaggacg aggaggagga ggaggcggcc gccggccagg ccaaggacga gctgtag      1257

<210> SEQ ID NO 2
<211> LENGTH: 1557
<212> TYPE: DNA
<213> ORGANISM: Artificial Sequence
<220> FEATURE:
<223> OTHER INFORMATION: The pcDNA3-CRT/HPV16E7 DNA vaccine is
      consisting of the coding sequences of a pcDNA3 vector and a CRT
      fused to a HPV16E7 protein
```

<400> SEQUENCE: 2

```
atgctgctcc ctgtgccgct gctgctcggc ctgctcggcc tggccgccgc cgagcccgtc    60
gtctacttca aggagcagtt tctggacgga gatgggtgga ccgagcgctg gatcgaatcc   120
aaacacaagt ccgattttgg caaattcgtc ctcagttcgg gcaagttcta cggcgatcag   180
gagaaagata aagggctgca gaccagccag gacgcccgct tctacgccct gtcggcccga   240
ttcgagccgt tcagcaacaa gggccagcca ctggtggtgc agttcaccgt gaaacacgag   300
cagaacattg actgcggggg cggctacgtg aagctgtttc cggccggcct ggaccagaag   360
gacatgcacg gggactctga gtacaacatc atgtttggtc ctgacatctg tggccccggc   420
accaagaagg ttcacgtcat cttcaactac aagggcaaga acgtgctgat caacaaggac   480
atccgttgca aggacgacga gttcacacac ctgtacacgc tgatcgtgcg gccggacaac   540
acgtatgagg tgaagattga acacagccag gtggagtcgg gctccctgga ggatgactgg   600
gacttcctac cccccaagaa gataaaggac ccagatgcct cgaagcctga agactgggac   660
gagcgggcca agatcgacga ccccacggac tccaagcccg aggactggga caagcccgag   720
cacatccccg acccggacgc gaagaagccc gaagactggg acgaagaaat ggacggagag   780
tgggagccgc cggtgattca gaaccccgag tacaagggtg agtggaagcc gcggcagatc   840
gacaaccccg attacaaagg cacctggatc caccccgaaa tcgacaaccc cgagtactcg   900
cccgacgcta acatctatgc ctacgacagc tttgccgtgc tgggcttgga cctctggcag   960
gtcaagtcgg gcaccatctt cgacaacttc ctcatcacca cgatgaggc gtacgcagag  1020
gagtttggca cgagacgtg gggcgtcacc aagacggccg agaagcagat gaaagacaag  1080
caggacgagg agcagcggct gaaggaggag gaggaggaga agaagcggaa ggaggaggag  1140
gaggccgagg aggacgagga ggacaaggac gacaaggagg acgaggatga ggacgaggag  1200
gacaaggacg aggaggagga ggaggcggcc gccggccagg ccaaggacga gctggaattc  1260
atgcatggag atacacctac attgcatgaa tatatgttag atttgcaacc agagacaact  1320
gatctctact gttatgagca attaaatgac agctcagagg aggaggatga aatagatggt  1380
ccagctggac aagcagaacc ggacagagcc cattacaata ttgtaacctt tgttgcaag  1440
tgtgactcta cgcttcggtt gtgcgtacaa agcacacacg tagacattcg tactttggaa  1500
gacctgttaa tgggcacact aggaattgtg tgccccatct gttctcagaa accataa    1557
```

<210> SEQ ID NO 3
<211> LENGTH: 1737
<212> TYPE: DNA
<213> ORGANISM: Artificial Sequence
<220> FEATURE:
<223> OTHER INFORMATION: The pcDNA3-CRT/HPV18E6 DNA vaccine is consisting of the coding sequences of a pcDNA3 vector and a CRT fused to a HPV18E6 protein.

<400> SEQUENCE: 3

```
atgctgctcc ctgtgccgct gctgctcggc ctgctcggcc tggccgccgc cgagcccgtc    60
gtctacttca aggagcagtt tctggacgga gatgggtgga ccgagcgctg gatcgaatcc   120
aaacacaagt ccgattttgg caaattcgtc ctcagttcgg gcaagttcta cggcgatcag   180
gagaaagata aagggctgca gaccagccag gacgcccgct tctacgccct gtcggcccga   240
ttcgagccgt tcagcaacaa gggccagcca ctggtggtgc agttcaccgt gaaacacgag   300
cagaacattg actgcggggg cggctacgtg aagctgtttc cggccggcct ggaccagaag   360
```

```
gacatgcacg gggactctga gtacaacatc atgtttggtc ctgacatctg tggccccggc    420
accaagaagg ttcacgtcat cttcaactac aagggcaaga acgtgctgat caacaaggac    480
atccgttgca aggacgacga gttcacacac ctgtacacgc tgatcgtgcg gccggacaac    540
acgtatgagg tgaagattga caacagccag gtggagtcgg gctccctgga ggatgactgg    600
gacttcctac cccccaagaa gataaaggac ccagatgcct cgaagcctga agactgggac    660
gagcgggcca agatcgacga ccccacggac tccaagcccg aggactggga caagcccgag    720
cacatccccg acccggacgc gaagaagccc gaagactggg acgaagaaat ggacggagag    780
tgggagccgc cggtgattca gaaccccgag tacaagggtg agtggaagcc gcggcagatc    840
gacaaccccg attacaaagg cacctggatc caccccgaaa tcgacaaccc cgagtactcg    900
cccgacgcta acatctatgc ctacgacagc tttgccgtgc tgggcttgga cctctggcag    960
gtcaagtcgg gcaccatctt cgacaacttc ctcatcacca cgatgaggc gtacgcagag   1020
gagtttggca cgagacgtg gggcgtcacc aagacggccg agaagcagat gaaagacaag   1080
caggacgagc agcagcggct gaaggaggag gaggaggaga gaagcggaa ggaggaggag   1140
gaggccgagg aggacgagga ggacaaggac gacaaggagg acgaggatga ggacgaggag   1200
gacaaggacg aggaggagga ggaggcggcc gccggccagg ccaaggacga gctggaattc   1260
atggcgcgct ttgaggatcc aacacggcga ccctacaagc tacctgatct gtgcacggaa   1320
ctgaacactt cactgcaaga catagaaata acctgtgtat attgcaagac agtattggaa   1380
cttacagagg tatttgaatt tgcatttaaa gatttatttg tggtgtatag agacagtata   1440
ccgcatgctg catgccataa atgtatagat tttattcta gaattagaga attaagacat   1500
tattcagact ctgtgtatgg agacacattg gaaaaactaa ctaacactgg gttatacaat   1560
ttattaataa ggtgcctgcg gtgccagaaa ccgttgaatc agcagaaaaa acttagacac   1620
cttaatgaaa aacgacgatt tcacaacata gctgggcact atagaggcca gtgccattcg   1680
tgctgcaacc gagcacgaca ggaacgactc caacgacgca gagaaacaca agtataa       1737

<210> SEQ ID NO 4
<211> LENGTH: 1554
<212> TYPE: DNA
<213> ORGANISM: Artificial Sequence
<220> FEATURE:
<223> OTHER INFORMATION: CRT/HPV16E7(detox) insert sequence of
      pNGVL4a-CRT/HPV16E7(detox) DNA vaccine sequence

<400> SEQUENCE: 4
atgctgctat ccgtgccgct gctgctcggc ctcctcggcc tggccgtcgc cgagcctgcc     60
gtctacttca aggagcagtt tctggacggg acgggtgga cttcccgctg gatcgaatcc    120
aaacacaagt cagattttgg caaattcgtt ctcagttccg gcaagttcta cggtgacgag    180
gagaaagata aggtttgca gacaagccag gatgcacgct tttatgctct gtcggccagt    240
ttcgagcctt tcagcaacaa aggccagacg ctggtggtgc agttcacggt gaaacatgag    300
cagaacatcg actgtggggg cggctatgtg aagctgtttc ctaatagttt ggaccagaca    360
gacatgcacg gagactcaga atacaacatc atgtttggtc ccgacatctg tggccctggc    420
accaagaagg ttcatgtcat cttcaactac aagggcaaga acgtgctgat caacaaggac    480
atccgttgca aggatgatga gtttacacac ctgtacacac tgattgtgcg gccagacaac    540
acctatgagg tgaagattga caacagccag gtggagtccg gctccttgga agacgattgg    600
gacttcctgc cacccaagaa gataaaggat cctgatgctt caaaaccgga agactgggat    660
```

```
gagcgggcca agatcgatga tcccacagac tccaagcctg aggactggga caagcccgag    720
catatccctg accctgatgc taagaagccc gaggactggg atgaagagat ggacggagag    780
tgggaacccc cagtgattca gaaccctgag tacaagggtg agtggaagcc ccggcagatc    840
gacaacccag attacaaggg cacttggatc cacccagaaa ttgacaaccc cgagtattct    900
cccgatccca gtatctatgc ctatgataac tttggcgtgc tgggcctgga cctctggcag    960
gtcaagtctg gcaccatctt tgacaacttc ctcatcacca cgatgaggc atacgctgag   1020 gagtttggca cgagacgtg gggcgtaaca aaggcagcag agaaacaaat gaaggacaaa   1080
caggacgagg agcagaggct aaggaggag gaagaagaca gaaacgcaa agaggaggag   1140 gaggcagagg acaaggagga tgatgaggac aaagatgagg atgaggagga tgaggaggac   1200
aaggaggaag atgaggagga agatgtcccc ggccaggcca aggacgagct ggaattcatg   1260
catggagata cacctacatt gcatgaatat atgttagatt tgcaaccaga gacaactgat   1320
ctctacggtt atgggcaatt aaatgacagc tcagaggagg aggatgaaat agatggtcca   1380
gctggacaag cagaaccgga cagagcccat tacaatattg taacctttg ttgcaagtgt   1440 gactctacgc ttcggttgtg cgtacaaagc acacacgtag acattcgtac tttggaagac   1500
ctgttaatgg gcacactagg aattgtgtgc cccatctgtt ctcagaaacc ataa          1554

<210> SEQ ID NO 5
<211> LENGTH: 1737
<212> TYPE: DNA
<213> ORGANISM: Artificial Sequence
<220> FEATURE:
<223> OTHER INFORMATION: CRT/HPV18E6 inserted sequence of
      pNGVL4a-CRT/HPV18E6 DNA vaccine

<400> SEQUENCE: 5
atgctgctcc ctgtgccgct gctgctcggc ctgctcggcc tggccgccgc cgagcccgtc     60
gtctacttca aggagcagtt tctggacgga gatgggtgga ccgagcgctg gatcgaatcc    120
aaacacaagt ccgattttgg caaattcgtc ctcagttcgg gcaagttcta cggcgatcag    180
gagaaagata agggctgca gaccagccag gacgcccgct ctacgccct gtcggcccga    240 ttcgagccgt tcagcaacaa gggccagcca ctggtggtgc agttcaccgt gaaacacgag    300
cagaacattg actgcggggg cggctacgtg aagctgtttc cggccggcct ggaccagaag    360
gacatgcacg gggactctga gtacaacatc atgtttggtc ctgacatctg tggccccggc    420
accaagaagg ttcacgtcat cttcaactac aagggcaaga acgtgctgat caacaaggac    480
atccgttgca aggacgacga gttcacacac ctgtacacgc tgatcgtgcg gccggacaac    540
acgtatgagg tgaagattga acagccag tggagtcgg gctccctgga ggatgactgg    600
gacttcctac cccccaagaa gataaaggac ccagatgcct cgaagcctga agactgggac    660
gagcgggcca agatcgacga ccccacggac tccaagcccg aggactggga caagcccgag    720
cacatccccg acccggacgc gaagaagccc gaagactggg acgaagaaat ggacggagag    780
tgggagccgc cggtgattca gaaccccgag tacaagggtg agtggaagcc gcggcagatc    840 gacaacccg attacaaagg cacctggatc caccccgaaa tcgacaaccc cgagtactcg    900
cccgacgcta acatctatgc ctacgacagc tttgccgtgc tgggcttgga cctctggcag    960
gtcaagtcgg gcaccatctt cgacaacttc ctcatcacca cgatgaggc gtacgcagag   1020 gagtttggca cgagacgtg gggcgtacc aagacggccg agaagcagat gaagacaag   1080 caggacgagg agcagcggct gaaggaggag gaggaggaga gaagcggaa ggaggaggag   1140
```

-continued

| | |
|---|---|
| gaggccgagg aggacgagga ggacaaggac gacaaggagg acgaggatga ggacgaggag | 1200 |
| gacaaggacg aggaggagga ggaggcggcc gccggccagg ccaaggacga gctggaattc | 1260 |
| atggcgcgct ttgaggatcc aacacggcga ccctacaagc tacctgatct gtgcacggaa | 1320 |
| ctgaacactt cactgcaaga catagaaata acctgtgtat attgcaagac agtattggaa | 1380 |
| cttacagagg tatttgaatt tgcatttaaa gatttatttg tggtgtatag agacagtata | 1440 |
| ccgcatgctg catgccataa atgtatagat ttttattcta gaattagaga attaagacat | 1500 |
| tattcagact ctgtgtatgg agacacattg gaaaaactaa ctaacactgg ttatacaat | 1560 |
| ttattaataa ggtgcctgcg gtgccagaaa ccgttgaatc cagcagaaaa acttagacac | 1620 |
| cttaatgaaa acgacgatt tcacaacata gctgggcact atagaggcca gtgccattcg | 1680 |
| tgctgcaacc gagcacgaca ggaacgactc caacgacgca gagaaacaca agtataa | 1737 |

<210> SEQ ID NO 6
<211> LENGTH: 2583
<212> TYPE: DNA
<213> ORGANISM: Artificial Sequence
<220> FEATURE:
<223> OTHER INFORMATION: CRT/E6E7L2 inserted sequence of
      pNGVL4a-CRT/E6E7L2 DNA vaccine

<400> SEQUENCE: 6

| | |
|---|---|
| atgctgctat ccgtgccgct gctgctcggc ctcctcggcc tggccgtcgc cgagcctgcc | 60 |
| gtctacttca aggagcagtt tctggacggg acgggtggga cttcccgctg gatcgaatcc | 120 |
| aaacacaagt cagattttgg caaattcgtt ctcagttccg gcaagttcta cggtgacgag | 180 |
| gagaaagata aggtttgca gacaagccag gatgcacgct tttatgctct gtcggccagt | 240 |
| ttcgagcctt tcagcaacaa aggccagacg ctggtggtgc agttcacggt gaaacatgag | 300 |
| cagaacatcg actgtggggg cggctatgtg aagctgtttc ctaatagttt ggaccagaca | 360 |
| gacatgcacg gagactcaga atacaacatc atgtttggtc ccgacatctg tggccctggc | 420 |
| accaagaagg ttcatgtcat cttcaactac aagggcaaga acgtgctgat caacaaggac | 480 |
| atccgttgca aggatgatga gtttacacac ctgtacacac tgattgtgcg gccagacaac | 540 |
| acctatgagg tgaagattga caacagccag gtggagtccg gctccttgga agacgattgg | 600 |
| gacttcctgc cacccaagaa gataaaggat cctgatgctt caaaaccgga agactgggat | 660 |
| gagcgggcca agatcgatga tcccacagac tccaagcctg aggactggga caagcccgag | 720 |
| catatccctg accctgatgc taagaagccc gaggactggg atgaagagat ggacggagag | 780 |
| tgggaacccc cagtgattca gaaccctgag tacaaggggt agtggaagcc ccggcagatc | 840 |
| gacaacccag attacaaggg cacttggatc cacccagaaa ttgacaaccc cgagtattct | 900 |
| cccgatccca gtatctatgc ctatgataac tttggcgtgc tgggcctgga cctctggcag | 960 |
| gtcaagtctg gcaccatctt tgacaacttc ctcatcacca acgatgaggc atacgctgag | 1020 |
| gagtttggca cgagacgtg gggcgtaaca aaggcagcag agaaacaaat gaaggacaaa | 1080 |
| caggacgagg agcagaggct taaggaggag gaagaagaca gaaacgcaa agaggaggag | 1140 |
| gaggcagagg acaaggagga tgatgaggac aaagatgagg atgaggagga tgaggaggac | 1200 |
| aaggaggaag atgaggagga gatgtccccc ggccaggcca aggacgagct ggaattcatg | 1260 |
| caccagaagc ggactgccat gttccaggac ccacaggagc gaccccggaa actgcctcag | 1320 |
| ctgtgcacag aactgcagac cacaatccat gatatcattc tggagtgcgt gtactgtaag | 1380 |
| cagcagctgc tgcggagaga ggtctatgat ttcgcctttc gcgacctgtg catcgtgtac | 1440 |

| | |
|---|---:|
| cgagacggca acccctatgc tgtcggggat aagtgcctga aattctacag taagatctca | 1500 |
| gaatatcggc actactgtta tagcctgtac gggactaccc tggagcagca gtataacaaa | 1560 |
| cctctgtgcg acctgctgat cagatgtatt aatggacaga agccctgtg ccctgaagag | 1620 |
| aaacagcggc acctggataa gaagcagaga tttcataaca tcagaggcag gtggaccggg | 1680 |
| agatgtatga gcacaaggcg cgagactcag ctgatgcacg gcgacactcc taccctgcat | 1740 |
| gaatatatgc tggacctgca gccagagaca actgatctgt acgggtatgg acagctgaac | 1800 |
| gattctagtg aagaggaaga tgagatcgac ggacctgctg gacaggcaga accagaccga | 1860 |
| gcacactaca atattgtgac attctgctgt aagtgcgata gtactctgag actgtgcgtg | 1920 |
| cagtcaaccc atgtcgatat caggacactg gaggacctgc tgatgggaac cctgggcatc | 1980 |
| gtggggccca tttgctccca gaagcctaaa agagcttctg caactcagct gtacaagacc | 2040 |
| tgcaaacagg cagggacatg tcctccagac atcattccca aggtggaggg aaaaactatc | 2100 |
| gccgatcaga ttctgcagta tggatctatg gcgtcttct ttggaggact gggaatcgga | 2160 |
| accggaagtg gaacaggagg caggactggg tacattccac tgggaacccg accacctaca | 2220 |
| gcaactgaca ccctggctcc tgtgcggcca ccactgacag tggaccccgt cggccccagc | 2280 |
| gacccttcca tcgtgtctct ggtcgaggaa ccagtttca ttgacgccgg cgctccaaca | 2340 |
| agtgtgccct caatccctcc agatgtcagc gggttttcca ttaccacatc tactgacact | 2400 |
| accccctgcta tcctggatat taacaatacc gtgacaactg tcaccacaca caacaatccc | 2460 |
| accttcaccg ccccctccgt gctgcagcca cctaccccag cagagacagg aggacatttc | 2520 |
| accctgagca gcagcactat cagcacccac aactacgaag aaatccctat ggacacttaa | 2580 |
| taa | 2583 |

<210> SEQ ID NO 7
<211> LENGTH: 2193
<212> TYPE: DNA
<213> ORGANISM: Artificial Sequence
<220> FEATURE:
<223> OTHER INFORMATION: sig/E7(detox)/HSP70 inserted sequence of
    pNGVL4a-sig/E7(detox)/HSP70 DNA vaccine

<400> SEQUENCE: 7

| | |
|---|---:|
| tcttatggcg gcccccggcg cccggcggcc gctgctcctg ctgctgctgg caggccttgc | 60 |
| acatggcgcc tcagcactct tgaggatct aatcatgcat ggagatacac ctacattgca | 120 |
| tgaatatatg ttagatttgc aaccagagac aactgatctc tacggttatg gcaattaaa | 180 |
| tgacagctca gaggaggagg atgaaataga tggtccagct ggacaagcag aaccggacag | 240 |
| agcccattac aatattgtaa ccttttgttg caagtgtgac tctacgcttc ggttgtgcgt | 300 |
| acaaagcaca cacgtagaca ttcgtacttt ggaagacctg ttaatgggca cactaggaat | 360 |
| tgtgtgcccc atctgttctc aaggatccat ggctcgtgcg gtcgggatcg acctcgggac | 420 |
| caccaactcc gtcgtctcgg ttctggaagg tggcgacccg gtcgtcgtcg ccaactccga | 480 |
| gggctccagg accaccccgt caattgtcgc gttcgcccgc aacggtgagg tgctggtcgg | 540 |
| ccagcccgcc aagaaccagg cggtgaccaa cgtcgatcgc accgtgcgct cggtcaagcg | 600 |
| acacatgggc agcgactggt ccatagagat tgacggcaaa aaatacaccg cgccggagat | 660 |
| cagcgcccgc attctgatga agctgaagcg cgacgccgag cctacctcg gtgaggacat | 720 |
| taccgacgcg gttatcacga cgcccgccta cttcaatgac gcccagcgtc aggccaccaa | 780 |
| ggacgccggc cagatcgccg cctcaacgt gctgcggatc gtcaacgagc cgaccgcggc | 840 |

```
cgcgctggcc tacggcctcg acaagggcga gaaggagcag cgaatcctgg tcttcgactt      900
gggtggtggc actttcgacg tttccctgct ggagatcggc gagggtgtgg ttgaggtccg      960
tgccacttcg ggtgacaacc acctcggcgg cgacgactgg gaccagcggg tcgtcgattg     1020
gctggtggac aagttcaagg gcaccagcgg catcgatctg accaaggaca agatggcgat     1080
gcagcggctg cgggaagccg ccgagaaggc aaagatcgag ctgagttcga gtcagtccac     1140
ctcgatcaac ctgccctaca tcaccgtcga cgccgacaag aacccgttgt tcttagacga     1200
gcagctgacc cgcgcggagt ccaacggat cactcaggac ctgctggacc gcactcgcaa      1260
gccgttccag tcggtgatcg ctgacaccgg catttcggtg tcggagatcg atcacgttgt     1320
gctcgtgggt ggttcgaccc ggatgcccgc ggtgaccgat ctggtcaagg aactcaccgg     1380
cggcaaggaa cccaacaagg gcgtcaaccc cgatgaggtt gtcgcggtgg agccgctct     1440 gcaggccggc gtcctcaagg gcgaggtgaa agacgttctg ctgcttgatg ttaccccgct     1500
gagcctgggt atcgagacca agggcggggt gatgaccagg ctcatcgagc gcaacaccac     1560
gatccccacc aagcggtcgg agactttcac caccgccgac gacaaccaac cgtcggtgca     1620
gatccaggtc tatcaggggg agcgtgagat cgccgcgcac aacaagttgc tcgggtcctt     1680
cgagctgacc ggcatcccgc cggcgccgcg ggggattccg cagatcgagg tcactttcga     1740
catcgacgcc aacggcattg tgcacgtcac cgccaaggac aagggcaccg gcaaggagaa     1800
cacgatccga atccaggaag gctcgggcct gtccaaggaa gacattgacc gcatgatcaa     1860
ggacgccgaa gcgcacgccg aggaggatcg caagcgtcgc gaggaggccg atgttcgtaa     1920
tcaagccgag acattggtct accagacgga gaagttcgtc aaagaacagc gtgaggccga     1980
gggtggttcg aaggtacctg aagacacgct gaacaaggtt gatgccgcgg tggcggaagc     2040
gaaggcggca cttggcggat cggatatttc ggccatcaag tcggcgatgg agaagctggg     2100
ccaggagtcg caggctctgg ggcaagcgat ctacgaagca gctcaggctg cgtcacaggc     2160
cactggcgct gcccaccccg gctcggctga tga                                 2193
```

<210> SEQ ID NO 8
<211> LENGTH: 2195
<212> TYPE: DNA
<213> ORGANISM: Artificial Sequence
<220> FEATURE:
<223> OTHER INFORMATION: Inserted sequence in TA-HPV

<400> SEQUENCE: 8

```
tttgaaaaac actatcttac tcatactcta gtttattatg agaaaaagta ccttataata      60
cgtagttggg ttatggtttc tgagaacaga tggggcacac aattcctagt gtgcccatta     120
acaggtcttc caaagtacga atgtctacgt gtgtgctttg tacgcacaac cgaagcgtag     180
agtcacactt gcaacaaaag gttacaatat tgtaatgggc tctgtccggt tctgcttgtc     240
cagctggacc atctatttca tcctcctcct ctgagctgtc atttaattgc cataaccgt      300 agagatcagt tgtctctggt tgcaaatcta acatatattc atgcaatgta ggtgtatctc     360
catgcatgat tcccagctgg gtttctctac gtgttcttga tgatctgcaa caagacatac     420
atcgaccggc ccaccgaccc cttatattat ggaatctttg cttttttgtcc agatgtcttt     480 gcttttcttc aggacacagt ggcttttgac agttaataca cctaattaac aaatcacaca     540
acggtttgtt gtattgctgt tctaatgttg ttccatacaa actataacaa taatgtctat     600
actcactaat tttagaataa aactttaaac atttatcaca tacagcatat ggattcccat     660
ctctatatac tatgcataaa tcccgaaaag caaagtcata tacctcacgt cgcagtaact     720
```

```
gttgcttgca gtacacacat tctaatatta tatcatgtat agttgtttgc agctctgtgc    780
ataactgtgg taactttctg ggtcgctcct gtgggtcctg aaacattgca gttctctttt    840
ggtccatggt ggttaacaaa gcttattacg atacaaactt aacggatatc gcgataatga    900
aataatttat gattatttct cgctttcaat ttaacacaac cctcaagaac ctttgtattt    960
attttcattt tttaagtata gaataaagaa tctataaaaa ctaaaaaaat tatacatcat   1020
aaaccaattt cctagttgtt tgtaagtcga cataccaata ctcaagacta cgaaactgat   1080
acaatctctt atcatgtggg taatgttctc gatgtcgata gccatatgcc cggtagttgc   1140
gatatacata aactgatcac taattccaaa cccacccgct ttttatagta agttttttcac  1200
ccataaataa taaatacaat aattaatttc tcgtaaaagt agaaaatata ttctaattta   1260
ttgcacggta aggaagtaga atcataaaga acagtactca atcaatagca atccatggcg   1320
cgctttgagg atccaacacg gcgaccctac aagctacctg atctgtgcac ggaactgaac   1380
acttcactgc aagacataga aataaacctgt gtatattgca agacagtatt ggaacttaca   1440
gaggtatttg aatttgcatt taaagattta tttgtggtgt atagagacag tataccgcat   1500
gctgcatgcc ataaatgtat agatttctac agtagaatca gagaattaag acattattca   1560
gactctgtgt atggagacac attggaaaaa ctaactaaca ctgggttata caatttatta   1620
ataaggtgcc tgcggtgcca gaaaccgttg aatccagcag aaaaacttag acacccttaat  1680
gaaaaacgac gatttcacaa catagctggg cactatagag gccagtgcca ttcgtgctgc   1740
aaccgagcac gacaggaacg actccaacga cgcagagaaa cacaagtagg aatattaagt   1800
atgcatggac ctaaggcaac attgcaagac attgtattgc atttagagcc ccaaaatgaa   1860
attccggttg accttctagg tcacgggcaa ttaagcgact cagaggaaga aaacgatgaa   1920
atagatggag ttaatcatca acatttacca gcccgacgag ccgaaccaca acgtcacaca   1980
atgttgtgta tgtgttgtaa gtgtgaagcc agaattgagc tagtagtaga aagctcagca   2040
gacgaccttc gagcattcca gcagctgttt ctgaacaccc tgtcctttgt gtgtccgtgg   2100
tgtgcatccc agcagtaacc cgggtacgta taatctggt agatagacca tcgaatgtat   2160
ttttttaact attacagaaa aaataacaaa tatgg                              2195
```

<210> SEQ ID NO 9  
<211> LENGTH: 9  
<212> TYPE: PRT  
<213> ORGANISM: Artificial Sequence  
<220> FEATURE:  
<223> OTHER INFORMATION: HPV16 E7aa49-57 peptide

<400> SEQUENCE: 9

Arg Ala His Tyr Asn Ile Val Thr Phe  
1               5

<210> SEQ ID NO 10  
<211> LENGTH: 9  
<212> TYPE: PRT  
<213> ORGANISM: Artificial Sequence  
<220> FEATURE:  
<223> OTHER INFORMATION: HPV18 E6aa67-75 peptide

<400> SEQUENCE: 10

Lys Cys Ile Asp Phe Tyr Ser Arg Ile  
1               5